United States Patent
Watanabe et al.

(10) Patent No.: US 9,752,112 B2
(45) Date of Patent: Sep. 5, 2017

(54) PRESSURE AND CIRCULATION CULTURE APPARATUS AND PRESSURE AND CIRCULATION CULTURE SYSTEM

(75) Inventors: Setuo Watanabe, Fuji (JP); Toshimi Murata, Fuji (JP); Mituharu Satou, Fuji (JP); Ibuki Kinouchi, Fuji (JP); Hidetada Takai, Fuji (JP)

(73) Assignee: PURPOSE CO., LTD., Fuji-shi, Shizuoka (JP)

( * ) Notice: Subject to any disclaimer, the term of this patent is extended or adjusted under 35 U.S.C. 154(b) by 0 days.

(21) Appl. No.: 13/403,186

(22) Filed: Feb. 23, 2012

(65) Prior Publication Data
US 2012/0156768 A1    Jun. 21, 2012

Related U.S. Application Data

(63) Continuation of application No. PCT/JP2010/006044, filed on Oct. 8, 2010.

(30) Foreign Application Priority Data

Oct. 9, 2009   (JP) .................... 2009-235291

(51) Int. Cl.
C12M 1/00      (2006.01)
C12M 1/42      (2006.01)

(52) U.S. Cl.
CPC ............ *C12M 29/14* (2013.01); *C12M 35/04* (2013.01)

(58) Field of Classification Search
CPC ....... C12M 21/08; C12M 29/10; C12M 29/12
(Continued)

(56) References Cited

U.S. PATENT DOCUMENTS 6,432,713 B2    8/2002   Takagi et al.
6,599,734 B2    7/2003   Takagi et al.
(Continued)

FOREIGN PATENT DOCUMENTS

CN    1737106 A     2/2006
EP    1266960 A1    12/2002
(Continued)

OTHER PUBLICATIONS

Notification of Transmittal of Copies of Translation of ther International Preliminary Report on Patentability of International Application No. PCT/JP2010/006044 mailed May 15, 2012 with Forms PCT/IB/373 and PCT/ISA/237, (7 pages). With English Translation.
(Continued)

*Primary Examiner* — William H Beisner
*Assistant Examiner* — Liban Hassan
(74) *Attorney, Agent, or Firm* — Westerman, Hattori, Daniels & Adrian, LLP

(57) ABSTRACT

The pressure and circulation culture apparatus includes a holder (culture chamber part), a pressure transmission part and a culture solution circulation line (culture circuit). The holder reserves culture solution and holds a cultured object. The pressure transmission part communicates with the holder and transmits an external pressure to the culture solution. The culture solution circulation line is connected to the holder via the pressure transmission part, and circulates the culture solution through the holder via the pressure transmission part. Such a structure is included, and an external pressure is made to operate on the culture solution via the pressure transmission part to allow pressure on the cultured object in the holder and circulation of the culture solution in the holder.

4 Claims, 24 Drawing Sheets

(58) Field of Classification Search
USPC .................................................. 435/289.1
See application file for complete search history.

(56) References Cited

U.S. PATENT DOCUMENTS

| | | | |
|---|---|---|---|
| 6,607,917 | B2 | 8/2003 | Takagi et al. |
| 6,921,662 | B2 | 7/2005 | Takagi et al. |
| 2001/0021529 | A1 | 9/2001 | Takagi |
| 2002/0037586 | A1* | 3/2002 | Takagi et al. ............... 435/395 |
| 2002/0098586 | A1 | 7/2002 | Takagi et al. |
| 2004/0077072 | A1 | 4/2004 | Takagi et al. |
| 2005/0069426 | A1 | 3/2005 | Mason et al. |
| 2006/0223047 | A1* | 10/2006 | Dancu et al. ............... 435/1.2 |
| 2007/0042490 | A1 | 2/2007 | Welter et al. |
| 2007/0269789 | A1* | 11/2007 | Covelli ............... A61F 2/2415 435/1.1 |
| 2008/0227189 | A1 | 9/2008 | Bader |
| 2009/0181448 | A1* | 7/2009 | Fan et al. ............... 435/284.1 |

FOREIGN PATENT DOCUMENTS

| | | |
|---|---|---|
| EP | 1382670 A1 | 1/2004 |
| EP | 1487264 | 12/2004 |
| JP | 2001-238663 A | 9/2001 |
| JP | 2002-315566 A | 10/2002 |
| JP | 2003-125755 A | 5/2003 |
| JP | 2003-289851 A | 10/2003 |
| JP | 2005-535293 A | 11/2005 |
| JP | 2006-000105 A | 1/2006 |
| JP | 2006000105 A * | 1/2006 |
| JP | 2006-325556 A | 12/2006 |
| WO | 01/64848 A1 | 9/2001 |
| WO | 03/080139 A2 | 10/2003 |
| WO | 2005/047466 A2 | 5/2005 |

OTHER PUBLICATIONS

International Search Report of PCT/JP2010/006044, mailing date Nov. 30. 2010.
Written Opinion of PCT/JP2010/006044, mailing date Nov. 30. 2010 in Japanese.
Australian Office Action dated Oct. 2, 2012, issued in corresponding Australian Patent Application No. 2010304580, (3 pages).
Chinese Office Action dated Dec. 26, 2012, issued in corresponding Chinese Patent Application No. 201080043973.3, w/ English translation.
Office Action dated Jul. 11, 2013 issued in corresponding Canadian Application No. 2,772,183.
Japanese Office Action dated Jan. 28, 2014, issued in corresponding Japanese Application No. 2009-235291, w/ English translation (6 pages).
Korean Office Action dated Feb. 6, 2014, issued in corresponding Korean Application No. 10-2012-7005900, w/ English translation (10 pages).
Canadian Office Action dated Feb. 19, 2014, issued in corresponding Canadian Application No. 2,772,183 (3 pages).
Extended European Search Report dated Apr. 10, 2015, issued in corresponding European Patent Application No. 10821759.7 (in English) (5 pages).
Chinese Office Action dated Jul. 2, 2015, issued in Chinese Patent Application No. 201410107310.3, a divisional application of counterpart Chinese Patent Application No. 201080043973.3; w/ partial English translation (14 pages).
Canadian Office Action dated Jun. 15, 2015, issued in counterpart Canadian application No. 2,772,183 (in English) (7 pages).
Canadian Office Action dated Jul. 6, 2016, issued in counterpart Canadian Patent Application No. 2,772,183 (5 pages, in English).

* cited by examiner (STRETCH OF SPRING)

(PRESSURE)

(RECIPROCATION OF PISTON)

(PRESSURE)

PRESSURE AND CIRCULATION CULTURE APPARATUS AND PRESSURE AND CIRCULATION CULTURE SYSTEM

CROSS-REFERENCE TO RELATED APPLICATIONS

This application is a continuation of International Application No. PCT/JP2010/006044, filed on Oct. 8, 2010, which is entitled to the benefit of priority of Japanese Patent Application No. 2009-235291, filed on Oct. 9, 2009, the contents of which are hereby incorporated by reference.

BACKGROUND OF THE INVENTION i) Field of the Invention

The present invention relates to culture techniques that are used for culture of cells and tissues of a living body, and for example, relates to a pressure and circulation culture apparatus and a pressure and circulation culture system which are used for culture research on cells and tissues and culture of tissues for treatment etc. The pressure and circulation culture apparatus and the pressure and circulation culture system can feed culture solution which is circulated to be supplied for a cultured object, and can pressure and stimulate a cultured object using the culture solution.

ii) Description of the Related Art

It has been put to practical use and is widely exploited to culture cells and tissues of a living body and to culture cells and tissues corresponding to a region of a living body.

Concerning a culture apparatus used for such culture, it is known to circulate culture solution and to pressure a cultured object using the circulated culture solution (for example, Japanese Laid-Open Patent Publication No. 2001-238663).

It is known that: plural solution feeding cylinders are connected with plural culture columns, respectively, to form a culture system having plural couples of a cylinder and a column; and one culture apparatus drives the plural solution feeding cylinders (for example, Japanese Laid-Open Patent Publication No. 2003-125755).

BRIEF SUMMARY OF THE INVENTION

Culture of a cultured object needs circulation and supply of culture solution, and physical stimulation. Supply of culture solution is solution feeding for supplying fresh culture solution to a cultured object. Physical stimulation is pressure through culture solution. Such solution feeding is to make culture solution flow, and such pressure is realized by elevation of a pressure of closed culture solution. Such solution feeding must be realized by a totally different structure from such pressure although an object for the solution feeding and pressure is culture solution. Conventionally, solution feeding is performed in a separate mechanism or part from pressure, and this fact leads to the problem of a complicated mechanism.

Using a single cultured object is rare. Rather, it is requested that a plurality of cultured objects are simultaneously cultured to compare culture transitions, and growth processes of the cultured objects. It is necessary that a plurality of culture apparatuses are installed and pieces of simultaneous culture under the same conditions is performed in such a case. However, there is the problem that it takes some time to set the same conditions when different culture apparatuses are juxtaposed.

An object of the pressure and circulation culture apparatus of the present invention is to simplify a mechanism of pressuring and circulating culture solution which is supplied to a cultured object.

An object of the pressure and circulation culture system of the present invention is to facilitate pieces of simultaneous culture of a plurality of cultured objects.

In order to achieve the above object, the pressure and circulation culture apparatus of the present invention includes a holder, a pressure transmission part and a culture solution circulation line. The holder is a means that reserves culture solution and that holds a cultured object. The pressure transmission part is a means that communicates with the holder and transmits an external pressure to the culture solution. The culture solution circulation line is a means that is connected to the holder via the pressure transmission part, and circulates the culture solution through the holder via the pressure transmission part. Such a structure is included in this pressure and circulation culture apparatus, and an external pressure is made to operate on the culture solution via the pressure transmission part to allow pressure on the cultured object in the holder and circulation of the culture solution in the holder.

In order to achieve the above object, the pressure and circulation culture system of the present invention is formed by a plurality of culture units each of which includes the holder, the pressure transmission part and the culture solution circulation line of the above described pressure and circulation culture apparatus, and the pressure and circulation culture system further includes a pressure drive part that generates an external pressure which is given to the pressure transmission part of each of the culture units. In such a pressure and circulation culture system, the external pressure generated by the pressure drive part is made to operate on the culture solution via the pressure transmission part to allow pressure on the cultured object in the holder of each of the culture units and circulation of the culture solution in the holder.

Other objects, features and advantages of the present invention will become clearer with reference to attached drawings and each embodiment.

DETAILED DESCRIPTION OF THE INVENTION

First Embodiment

In a first embodiment, a holder holding a cultured object communicates with a pressure transmission part, and an external pressure on the pressure transmission part is transmitted to culture solution.

Figure 1:
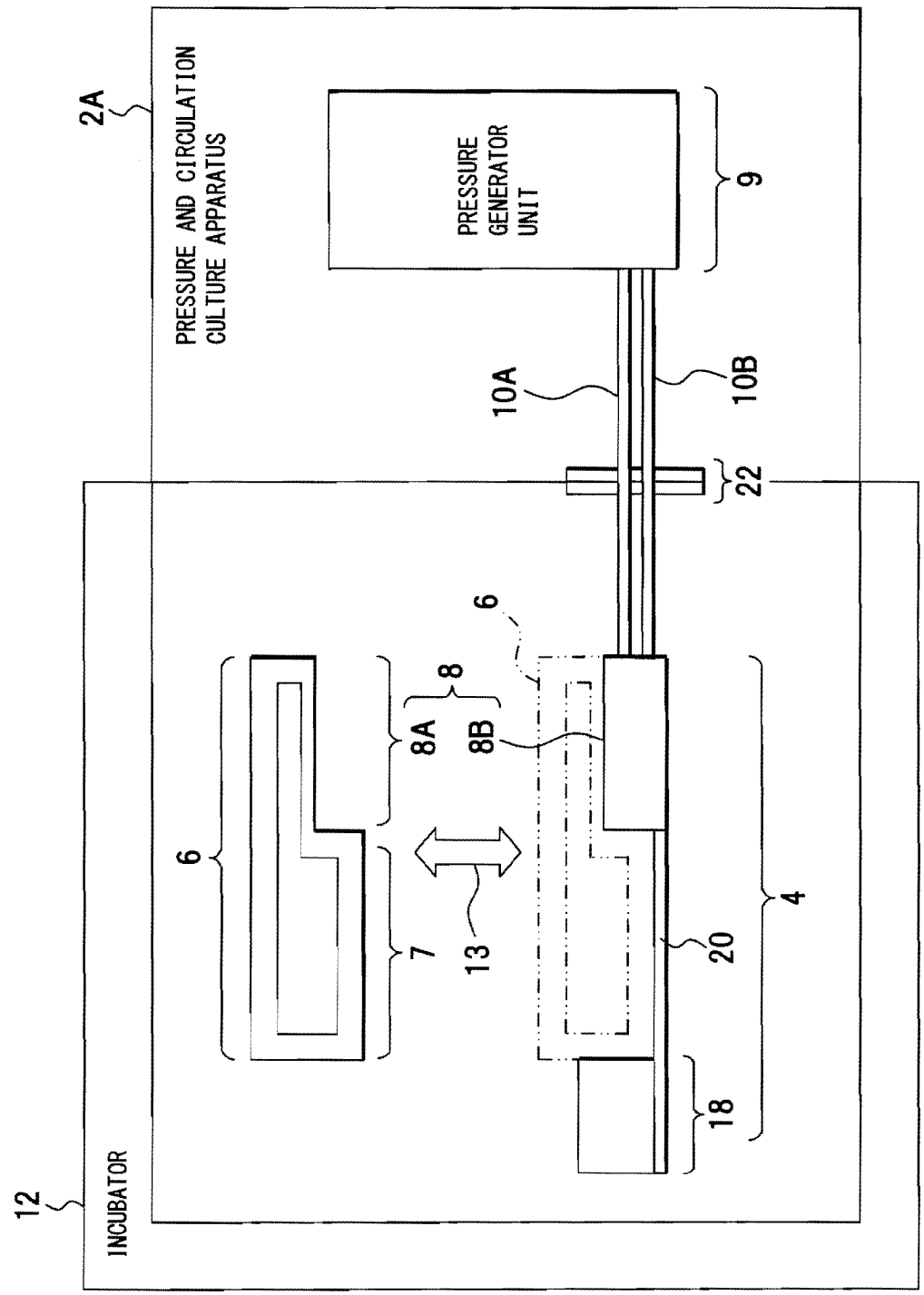
FIG. 1 depicts an example of a pressure and circulation culture apparatus according to a first embodiment.

The first embodiment will be described with reference to FIG. 1. FIG. 1 depicts an example of a pressure and circulation culture apparatus according to the first embodiment.

This pressure and circulation culture apparatus 2A is an example of the pressure and circulation culture apparatus of the present invention. The pressure and circulation culture apparatus 2A includes, as function parts, a culture unit 4, a culture unit main body 6, a culture chamber part 7, a pressure transmission part 8, a pressure generator unit 9, pressure piping 10A and 10B and an incubator 12.

The culture unit 4 is a culture means that supplies culture solution 14 (FIG. 2) and transmits a pressure, which is generated by the pressure generator unit 9, to the culture chamber part 7. The culture unit 4 has the culture unit main body 6 detachably. The culture unit main body 6 has the culture chamber part 7 and a pressure transmission part 8A of a culture solution side in the pressure transmission part 8.

The culture chamber part 7 is an example of a holder that holds a cultured object. The culture chamber part 7 is a means that holds, for example, a three-dimensional structure to differentiate and proliferate cells, and to produce extracellular matrixes. This three-dimensional structure is formed by cells or by cells and a scaffold as a cultured object that is made of cells or tissues of a living body. The culture chamber part 7 can be attached to and detached from the pressure transmission part 8 as depicted by an arrow 13. The culture chamber part 7 is disposed in the incubator 12 along with the culture unit 4 in this embodiment.

The pressure transmission part 8 includes the above described pressure transmission part 8A of a culture solution side and a pressure transmission part 8B of a pressure medium side. For example, the pressure transmission part 8 transmits a pressure generated by the pressure generator unit 9, from the pressure transmission part 8A of a culture solution side to the culture chamber part 7 via the pressure transmission part 8B of a pressure medium side. The pressure transmission part 8B of a pressure medium side and a shut-off valve drive unit 18 which is for opening and closing the culture chamber part 7 are coupled via a coupling part 20.

Figure 2:
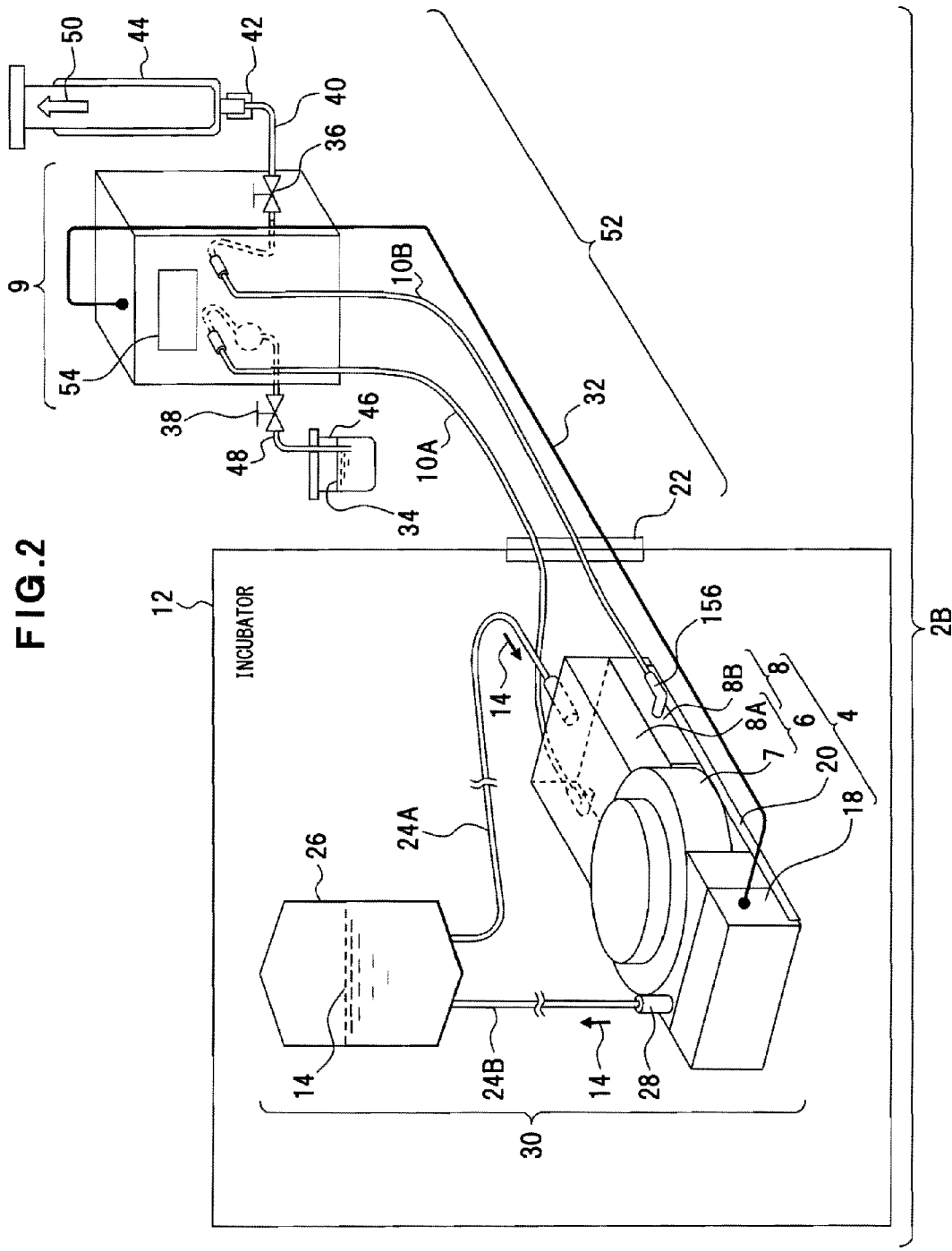
FIG. 2 depicts an example of a pressure and circulation culture apparatus according to a second embodiment.

The pressure generator unit 9 is an example of a pressure generation source and a pressure generation means for generating a pressure on the culture chamber part 7 and a pressure for circulation of the culture solution 14 (FIG. 2). The pressure generator unit 9 outputs the generated pressure to the pressure piping 10A and 10B.

The pressure piping 10A and 10B is an example of a pressure transmission pipe. A tube that has pressure resistance, heat resistance and flexibility may be used for the pressure piping 10A and 10B. For example, the pressure piping 10A and 10B is made from a pressure resistant tube. A pressure generated by the pressure generator unit 9 is applied to the pressure transmission part 8 through the pressure piping 10A and 10B.

The incubator 12 is an example of a culture chamber, and has airtightness of shut-off from the outside. The incubator 12 includes a penetration part 22 so that the pressure piping 10A and 10B penetrates therethrough. The penetration part 22 includes a sealing for sealing the incubator 12. In this embodiment, a pair of the pressure piping 10A and 10B is used, and the pressure applied to the pressure transmission part 8 through the pressure piping 10A from the pressure generator unit 9 is returned to the pressure generator unit 9 through the pressure piping 10B. Single pressure piping 10 may be used instead of such a structure.

With such a structure, a pressure generated by the pressure generator unit 9 is applied to the pressure transmission part 8 from the pressure piping 10A and 10B, and then is applied to a cultured object in the culture chamber part 7 from this pressure transmission part 8. Culture solution can be circulated through the culture chamber part 7 in response to the pressure applied to the pressure transmission part 8.

Second Embodiment

A second embodiment discloses an example of a structure of embodying the above described function parts according to the first embodiment.

The second embodiment will be described with reference to FIG. 2. FIG. 2 depicts an example of a pressure and circulation culture apparatus according to the second embodiment. In FIG. 2, the same parts as those of FIG. 1 are denoted by the same reference numerals.

This pressure and circulation culture apparatus 2B includes a culture unit 4 as a culture unit that has a culture circuit 30 of a closed system. The culture circuit 30 is formed by a culture chamber part 7 where a cultured object 62 (FIG. 4) is held, culture solution piping 24A and 24B which is an example of culture solution circulation lines, and a culture solution reservoir 26. In this case, a culture unit main body 6 also forms a detachable unit. The culture circuit 30 is filled with the culture solution 14. The culture chamber part 7 is connected with the pressure transmission part 8, and disposed in the incubator 12. Connection of the pressure transmission part 8 with the pressure generator unit 9 via the pressure piping (for example, pressure resistant tubes) 10A and 10B forms a pressure circuit 52. This pressure circuit 52 is filled with pressure medium (water or the like) 34. The pressure piping 10B is connected to the pressure transmission part 8B of a pressure medium side via a port part 156, for example. A pressurized water block valve 36 is disposed at the pressure generator unit 9 side. The pressurized water block valve 36 may be disposed at the incubator 12 side so that the pressure medium 34 is not returned to the pressure generator unit 9.

The culture circuit 30, the shut-off valve drive unit 18 and the pressure transmission part 8 are disposed in the incubator 12. The pressure piping 10A and 10B, and a shut-off valve drive wiring 32 penetrate through the penetration part 22 of the incubator 12. A sealing process is executed for this penetration part 22. This sealing process minimizes consumption of nitrogen and carbon dioxide in the incubator 12.

The culture solution reservoir 26 is connected to the culture unit 4 via the culture solution piping 24A and 24B. The culture solution 14 is injected from this culture solution reservoir 26 via the culture solution piping 24A. The culture unit main body 6 is coupled with a culture solution discharge part 28. The culture solution 14 which has been circulated through the culture unit main body 6 is returned to the culture solution reservoir 26 from the culture solution discharge part 28 via the culture solution piping 24B. The culture circuit 30 is formed like the above as a circuit for circulating the culture solution 14 therearound to culture a cultured object in the culture unit main body 6. In this case, the culture solution 14 which has been circulated through the culture unit main body 6 may be discharged somewhere except the culture solution reservoir 26 without the return to the culture solution reservoir 26.

The shut-off valve drive wiring 32 is connected to the shut-off valve drive unit 18. This shut-off valve drive wiring 32 is introduced to the outside of the incubator 12 through the penetration part 22 to be connected to the pressure generator unit 9 side. The shut-off valve drive unit 18 is a driving means for driving a shut-off valve into "close" when a pressure is applied and into "open" when the culture solution 14 is circulated. It is desirable to normally close, that is, to "close" a shut-off valve when energization is not executed, for minimizing heat generation from a driving means. In this embodiment, a control means for the shut-off valve drive unit 18 is built in the pressure generator unit 9.

The incubator 12 forms an optimal environmental chamber for realizing an optimal environment suitable for culture of a cultured object. Optimal oxygen concentration, carbon dioxide concentration, temperature, and humidity are set for the incubator 12.

The pressure generator unit 9 makes a generated pressure operate on the pressure transmission part 8 using the pressure medium 34, e.g., pressurized water through the pressure piping 10A and 10B. Pressurized water block valves 36 and 38 are connected to the pressure generator unit 9. These pressurized water block valves 36 and 38 are disposed at an outlet and an inlet for the pressure medium 34, respectively, and are means for closing the pressure medium 34 that has been injected. These pressurized water block valves 36 and 38 are opened, the pressure medium 34 in a vessel 46 is introduced to the pressure generator unit 9 via a tube 48 by using a syringe 44 as an suction means which is connected to the tube 40 via a luer connector 42 or the like, and further the pressure medium 34 is introduced into the pressure piping 10A and 10B. An arrow 50 indicates a direction where a piston of the syringe 44 travels when the pressure medium 34 is drawn. Thus, the pressure circuit 52 is formed by the pressure generator unit 9, the pressure piping 10A and 10B, and the pressure transmission part 8. Asepsis is not needed for this portion.

A display part 54 for visually displaying input information and output information is disposed on the pressure generator unit 9.

Figure 3:
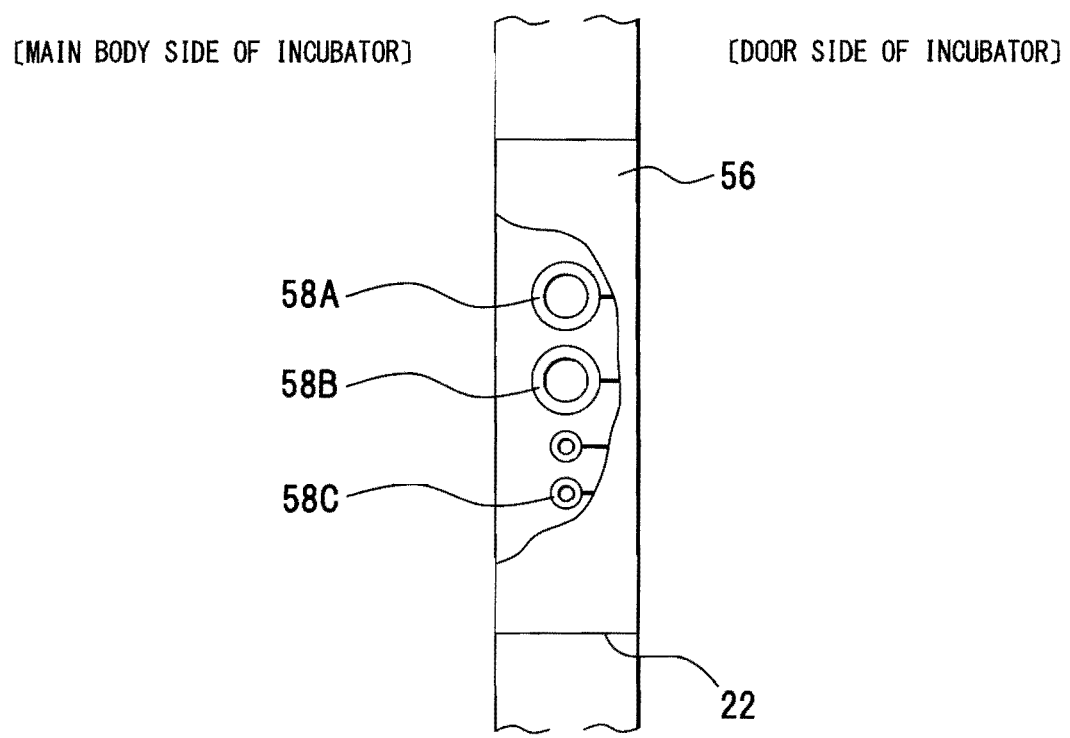
FIG. 3 depicts an example of a penetration part of an incubator.

For the penetration part 22, for example as depicted in FIG. 3, a door packing 56 that divides the main body side and door side of the incubator 12 is disposed. Penetration parts 58A and 58B for the pressure piping 10A and 10B, a penetration part 58C through which the shut-off valve drive wiring 32 penetrates, etc. are disposed in this door packing 56. The penetration parts 58A, 58B and 58C may be formed through a sealing for a penetration part that is provided for the door packing 56.

Figure 4:
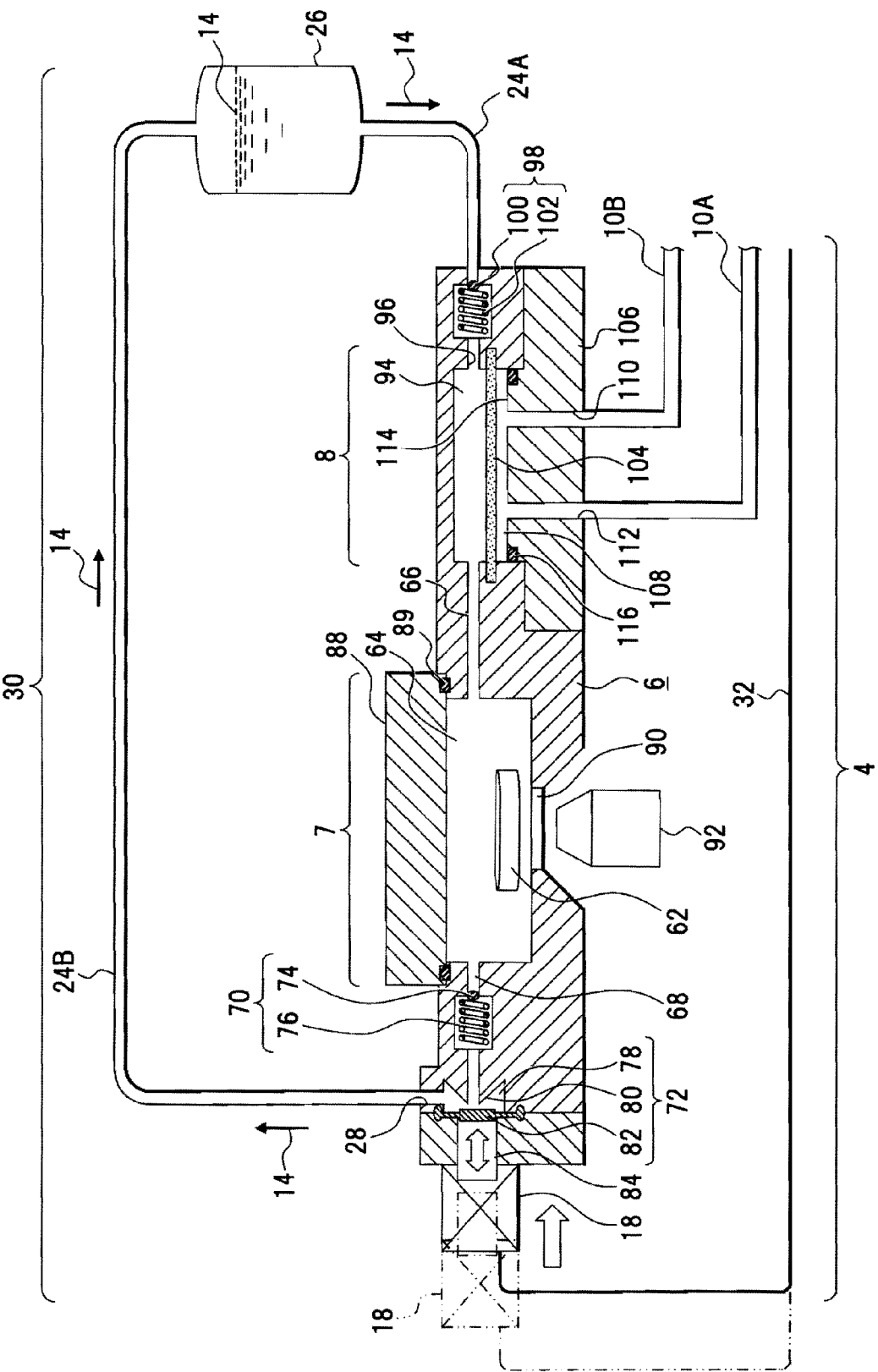
FIG. 4 depicts an example of a culture unit.

The culture unit 4 will be described with reference to FIG. 4. FIG. 4 depicts an example of the culture unit. In FIG. 4, the same parts as those of FIGS. 1 and 2 are denoted by the same reference numerals.

The culture unit main body 6 is provided for this culture unit 4. For example, this culture unit main body 6 is formed by a corrosion-resistant material such as stainless steel that does not demonstrate toxicity against a living body. This culture unit main body 6 provides the culture chamber part 7 and the pressure transmission part 8.

The culture unit main body 6 is a pressure resistant container to which a pressure can be transmitted. A sealing cover 88, a pressure transmission film 104, and a valve part 82 of a shut-off valve part 72 are attached to the culture unit main body 6. The culture unit main body 6 includes the culture circuit 30 for the culture solution 14 that is formed by a culture solution bag which is the culture solution reservoir 26, and the culture solution piping 24A and 24B such as silicone tubes to be a hermetically closed culture circuit of a closed system.

A holding space 64 where the cultured object 62 is held is formed in the culture chamber part 7. This holding space 64 is a cylindrical shape. Passages 66 and 68 are formed from this holding space 64 in the diameter direction. The passage 66 communicates with the pressure transmission part 8, and the passage 68 communicates with the culture solution piping 24B. The culture chamber part 7 and the sealing cover 88 are sealed with a sealant 89.

The holding space 64 is a portion that holds a three-dimensional structure formed by cells or by cells and a scaffold as the cultured object 62 to differentiate and proliferate cells, to produce extracellular matrixes, etc. In culture, the culture chamber part 7 is disposed in the incubator 12 or a constant temperature bath whose environment of temperature, oxygen concentration, carbon dioxide concentration, etc. has been arranged. The incubator 12 may not be used when, for example, cells of a poikilotherm are cultured.

A check valve 70 and the shut-off valve part 72 are provided for the passage 68 side. The check valve 70 is a second valve that shuts off the circulation of the culture solution 14 discharged from the holding space 64 of the culture chamber part 7 which is a holder, to check a backflow of the culture solution 14. The check valve 70 is disposed at the outlet for culture solution at the downstream side of the culture chamber part 7. The check valve 70 is formed by a ball valve 74 and a spring 76. Restoring force of the spring 76 which is in a compressed state operates on the ball valve 74. A solution pressure that overcomes pressing force of the spring 76 is necessary for the flow of the culture solution 14 into the passage 68. This check valve 70 may not be necessary disposed.

The shut-off valve part 72 includes a valve chest 78 that communicates with the passage 68, a truncated cone-shaped valve seat 80 that is projected into this valve chest 78, and the valve part 82 made from an elastic body that abuts this valve seat 80. A plunger 84 that the shut-off valve drive unit 18 provides is attached to this valve part 82. The shut-off valve drive unit 18 reciprocates the plunger 84 in response to an electric signal to open and close the valve part 82 for the valve seat 80. The culture solution piping 24B is connected to the culture solution discharge part 28 in the valve chest 78. When the shut-off valve part 72 is opened, the culture solution 14 can flow out of the valve chest 78 to the culture solution piping 24B side.

The openable and closable sealing cover 88 is disposed on the culture chamber part 7, and maintains the sealed state of the culture circuit 30. An inspection window 90 is formed on the bottom of the culture chamber part 7. This inspection window 90 is blocked by a transparent material. The inspection window 90 is a small window for inspecting the state of inside cells etc. while a pressure is applied or pressure application is suspended. The inspection window 90 is made from a sufficiently pressure resistant, less-deformable, and transparent material that does not have an adverse effect on microscope inspection such as quartz and an artificial sapphire. For example, a microscope eyepiece 92 is disposed over this inspection window 90, and the status of the cultured object 62 can be inspected from the outside. The sealing cover 88 is a cover for closing the holding space 64. It is preferable that the sealing cover 88 is made from a transparent material that can introduce light to the culture chamber part 7 for microscope inspection.

A pressure transmission space 94 is formed in the pressure transmission part 8 as a culture solution reservoir for reserving the culture solution 14 and transmitting a pressure to the culture solution 14. The pressure transmission space 94 is an oblong cylindrical shape. The above described passage 66 and a passage 96 are formed from the pressure transmission space 94 in the diameter direction. This passage 96 provides a check valve 98, and the culture solution piping 24A is connected to the passage 96. This check valve 98 is a first valve that shuts off the circulation of the culture solution 14 to check the back flow of the culture solution 14 from the pressure transmission space 94 to the culture solution piping 24A. The check valve 98 is attached to the inlet for culture solution at the upstream side of the pressure transmission part 8, and formed by a ball valve 100 and a spring 102. Restoring force of the spring 102 which is in a compressed state operates on the ball valve 100. A solution pressure that overcomes pressing force of the spring 102 is necessary for the flow of the culture solution 14 into the passage 96.

The pressure transmission film 104 that closes the pressure transmission space 94 is disposed in this pressure transmission part 8. A pressure medium space 108 is formed between the pressure transmission film 104 and a joint part 106. This pressure medium space 108 is an example of an external pressure operation part for making a pressure from the outside of the incubator 12 operate via a pressure transmission medium. The pressure transmission film 104 is an example of a pressure transmission film that transmits an external pressure to the culture solution 14. The pressure transmission film 104 is also a function part that hermetically seals the culture chamber part 7 and the pressure transmission space 94 and that transmits the pressure from the pressure generator unit 9 to the holding space 64. A thin elastomeric film or plastic film may be used for this pressure transmission film 104. A pressure is transmitted to the pressure transmission space 94 with little change if this pressure transmission film 104 is in a flexible state where a tensile strength can be almost ignored when the pressure transmission film 104 is attached. A pressure of the pressure transmission space 94 which is divided by the pressure transmission film 104 is transmitted to the holding space 64. Even if a pressure difference generates a tensile strength, a culture program may be set so that a tensile strength can be ignored.

The joint part 106 is a means for transmitting the pressure generated by the pressure generator unit 9, to the culture chamber part 7. The joint part 106 is attachable to and detachable from the culture unit main body 6. The pressure transmission space 94 contacts the pressure medium space 108 via the pressure transmission film 104. The joint part 106 is a blocking means that blocks the pressure medium space 108, and a means that makes the pressure from the pressure piping 10A and 10B operate on the pressure transmission film 104. This joint part 106 is fitted to the culture chamber part 7, and transmits the pressure generated by the pressure generator unit 9 to the culture chamber part 7. In this case, a flexible and pressure resistant tube of approximately 5 mm or below in inside diameter may be used for the pressure piping 10A and 10B. A thin pipe does not stop the air on the way, and improves pressure resistance. The pressure piping 10A and 10B is connected to port parts 112 and 110 of the joint part 106, respectively. An insertion part 114 for insertion to the pressure medium space 108 is formed for the joint part 106. A sealant 116 for maintaining the airtightness of the pressure medium space 108 is provided for this insertion part 114. This sealant 116 keeps the airtightness of a connection part between the joint part 106 and the pressure transmission part 8 to allow pressure transmission.

The pressure medium space 108 is a space that is made when the pressure transmission part 8 is fitted. This portion is filled with the pressure medium 34. The clearance in the pressure medium space 108 is minimized (4 mm or below) in order to reduce remaining air to the utmost. This minimization facilitates the discharge of the air, and does not allow the air to remain. The pressure on this portion is transmitted to the pressure transmission space 94 via the pressure transmission film 104. Asepsis is required for this portion because the inside of this portion touches the culture solution 14 and cell tissue.

Figure 5:
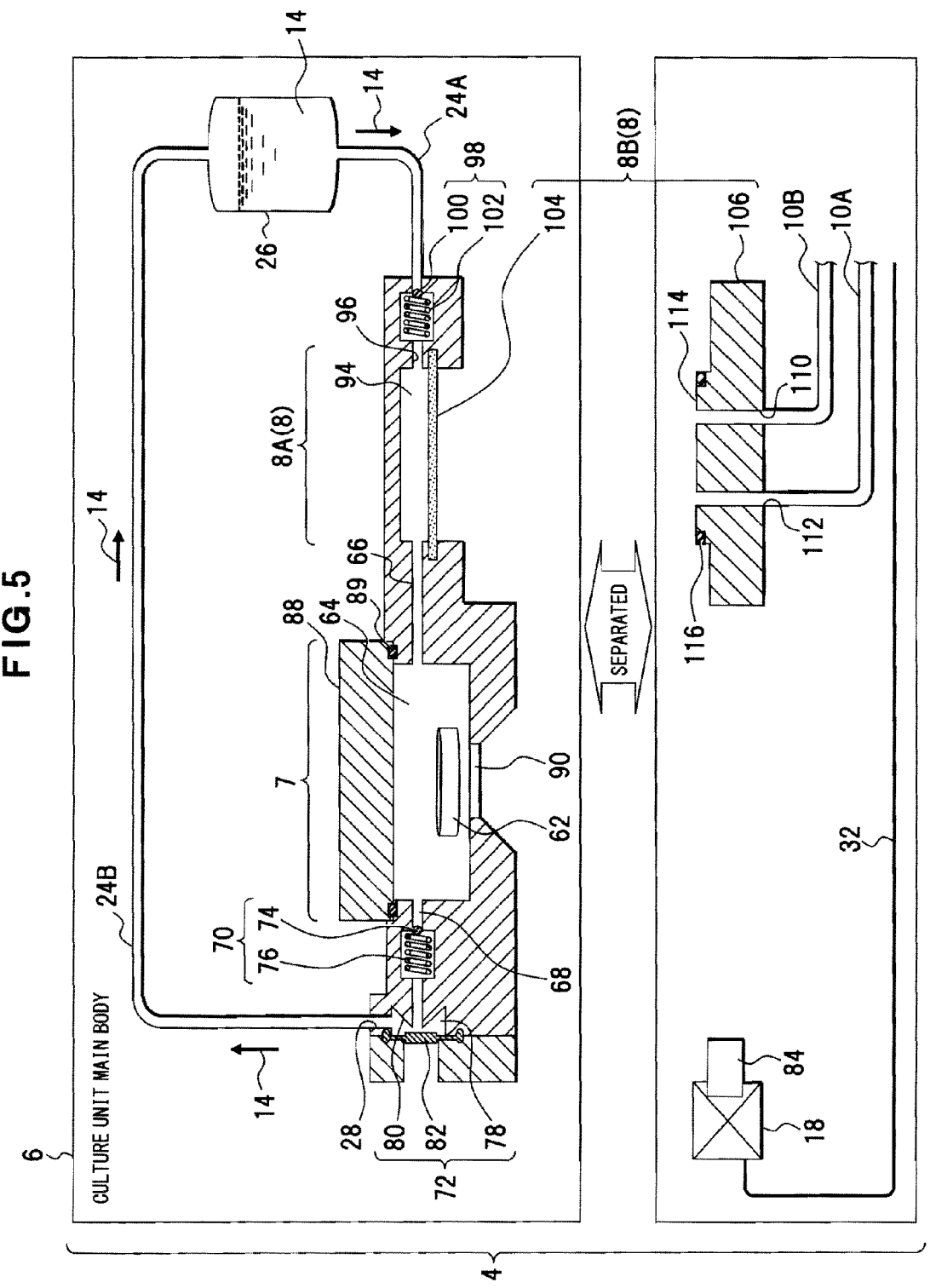
FIG. 5 depicts separation of a culture unit main body, and a shut valve drive unit and a joint part.

In the culture unit 4 of such a structure, as depicted in FIG. 5, the culture unit main body 6 can be separated from or combined with the joint part 106 and the shut-off valve drive unit 18 if necessary. Because the check valves 70 and 98 are means for preventing the culture solution 14 from flowing back, a solenoid valve that can prevent a backflow may be used, a so-called check valve may be used, or both of them may be used for the check valves 70 and 98. In culture, the shut-off valve part 72 is opened and closed by the shut-off valve drive unit 18 at the side of the outlet for culture solution.

Figure 6:
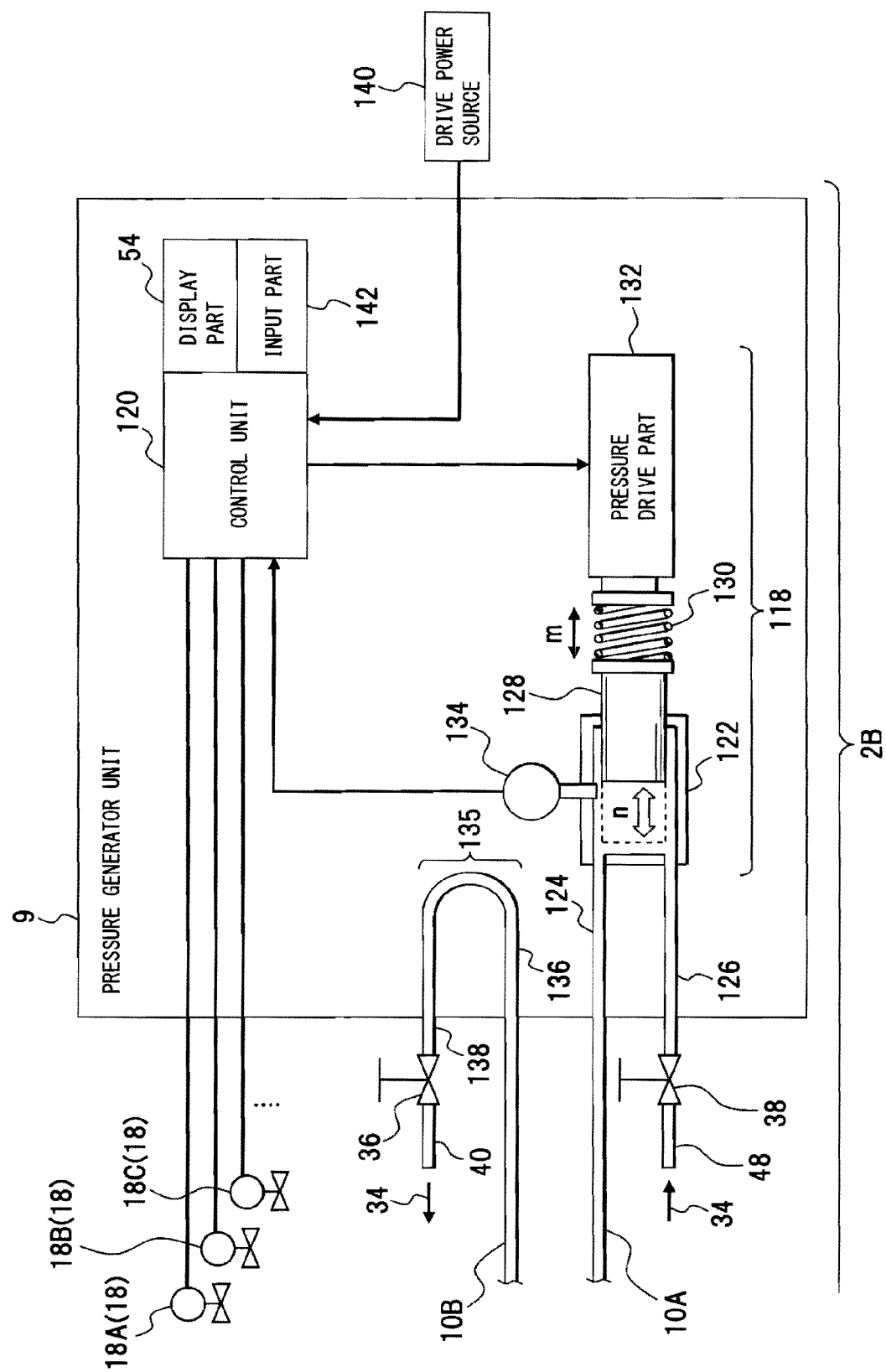
FIG. 6 depicts an example of a pressure generator unit.

The pressure generator unit 9 will be described with reference to FIG. 6. FIG. 6 depicts an example of the pressure generator unit. In FIG. 6, the same parts as those of FIGS. 1, 2 and 4 are denoted by the same reference numerals.

The pressure generator unit 9 is a drive source for the operation according to a pressure value and the volume of circulating culture solution which have been set. A pressure device 118 and a control unit 120 are provided for this pressure generator unit 9. A cylinder 122 is disposed in the pressure device 118 as a pressure vessel. This cylinder 122 holds the pressure medium 34, keeps a pressure generated by the operation of a piston 128, and transmits the pressure to the pressure transmission part 8. Port parts 124 and 126 are formed in this cylinder 122, and the piston 128 is provided for the cylinder 122. The piston 128 compresses the pressure medium 34 in the cylinder 122, which is as a pressure vessel, applies or reduces the pressure of the cylinder 122, and also plays as a pump when the culture solution 14 is circulated. The pressure medium 34 may be fluid such as water and oil. The pressure piping 10A is connected to the port part 124, and the tube 48 is connected to the port part 126. The pressure piping 10A and 10B is piping for transmitting the pressure in the cylinder 122 to the culture chamber part 7. The pressure piping 10A and 10B is a pressure resistant and flexible pipe for filling with the pressure medium 34. A pressure drive part 132 is coupled to the piston 128 via a spring 130. The pressure drive part 132 is a driving means for reciprocating the piston 128. The pressure drive part 132 receives a control output from the control unit 120, and generates driving force that moves the piston 128 in the direction where a pressure is applied to the cylinder 122 and moves the piston 128 in the direction where the pressure in the cylinder 122 is reduced.

The spring 130 is compressed by the driving force in the direction of applying a pressure to generate reaction, and the compression is released by the driving force in the direction of reducing a pressure. That is, the reaction when the spring 130 is compressed is transmitted to the pressure medium in the cylinder 122 via the piston 128 as a pressure. An arrow m represents the amount of the compression of the spring 130 and an arrow n represents the travel distance of the piston 128. The pressure drive part 132 includes a drive unit such as a stepping motor to compress the spring 130. The inclusion of the spring 130 widens the range of the operation of a motor etc., facilitates pressure control, and improves accuracy. A servomotor, output from which can be adjusted, etc. may be used instead of this spring 130 to adjust the output of the pressure drive part 132 to adjust the pressing force of the piston 128.

This spring 130 facilitates the control of a pressure because the amount of the compression thereof is relative to compressive force, that is, the pressure transmitted to fluid. If pressure and circulation culture is performed under low pressure like blood pressure, a set of a pressure sensor which is dimensionally compatible and whose maximum measurable pressure is low, and a spring which is dimensionally compatible and has a small spring constant is exchanged. For example, a pressure sensor 134 of 1 MPa in full scale is changed to that of 100 kPa, and a spring is changed to that of a tenth in spring constant. In this case, an indicated value may read as a tenth (for example, the indication of 0.5 MPa is changed to read as 50 kPa). Alternatively, it may be inputted from an input part 142 that components for low pressure are used, to indicate correct pressure indication by an operation program according to the input. A torque-adjustable servo motor may be used to omit a spring.

The above described pressure sensor 134 is disposed at the cylinder 122. The pressure value detected by the pressure sensor 134 is transmitted to the control unit 120. The pressure sensor 134 performs sensing of the pressure in the cylinder 122. Every continuous place has the same pressure in still fluid. Thus, the cylinder 122 is equal to the culture chamber part 7 in pressure, and by pressure measurement in the cylinder 122, the pressure in the culture chamber part 7 can be known indirectly without contact with the culture solution 14. The pressure sensor 134 may be selected according to a pressure to be applied.

A pressure piping part 135 is disposed at the position which is adjacent to the cylinder 122. The pressure piping 10B is connected to one port part 136 and the tube 40 is connected to another port part 138 of this pressure piping part 135.

To the control unit 120, power is supplied from a drive power source 140 and a (operation) setting value is inputted from the input part 142. Thus, the above described control output for the pressure drive part 132 is generated, and control output for the shut-off valve drive units 18A, 18B and 18C is generated. That is, the control unit 120 is a means for controlling driving while performing pressure sensing according to setting input. Juxtaposition of a plurality of culture units 4 is assumed, and control output for each of a plurality of the shut-off valve drive units 18A, 18B and 18C can be generated in the pressure generator unit 9 in this embodiment. Setting input is applied to this control unit 120 from the input part 142 and the control unit 120 obtains display output for the display part 54. Setting information such as pressure intensity, a pressure cycle and the volume of circulating culture solution is inputted from the input part 142. Input and output information such as an input value and a pressure value during pressure operation is displayed on the display part 54.

Figure 7:
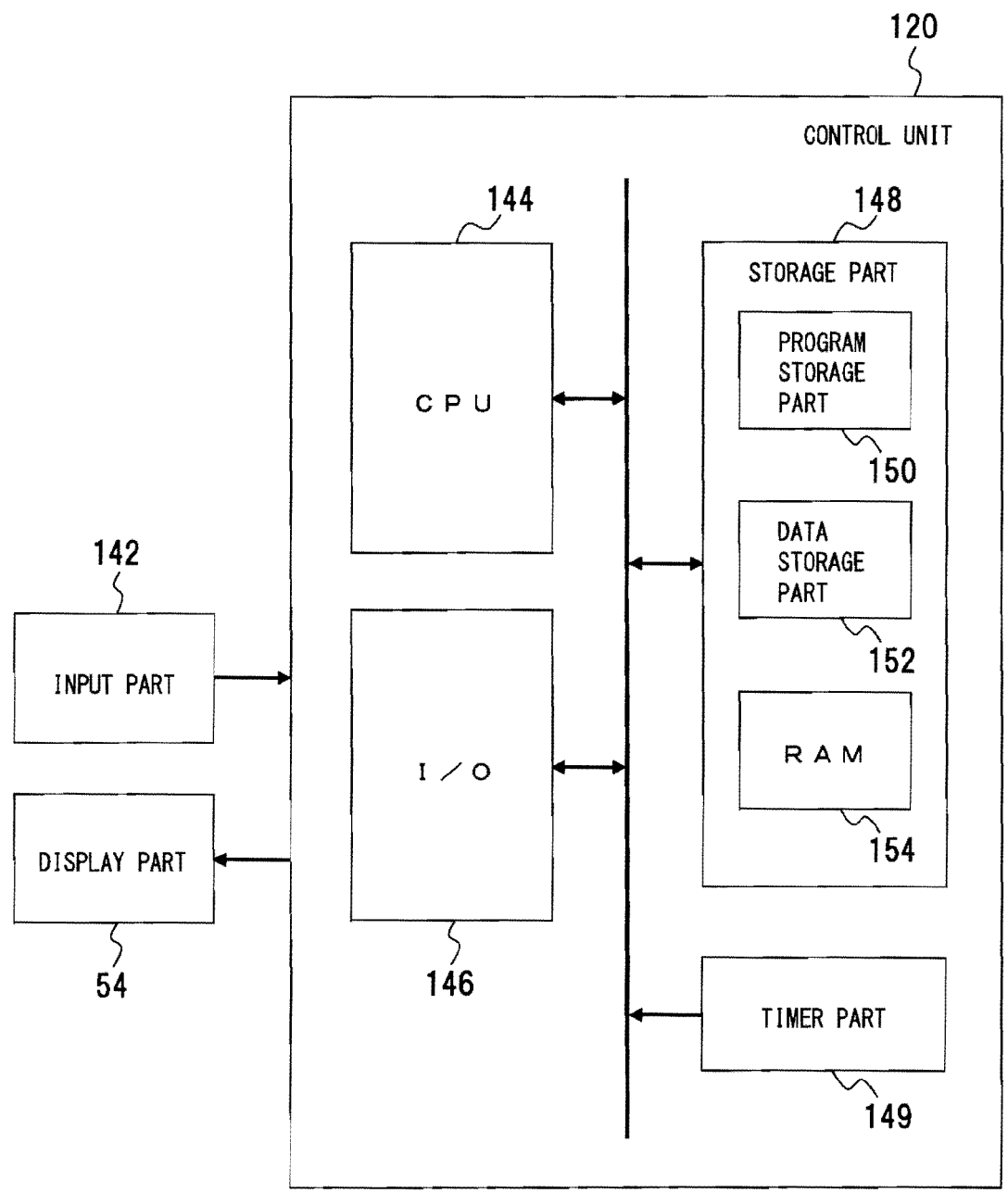
FIG. 7 depicts an example of a control unit.

The control unit 120 includes, as depicted in FIG. 7 for example, a CPU (Central Processing Unit) 144, an input and output part (I/O) 146, a storage part 148, and a timer part 149. The CPU 144 executes control of various function parts and reading out and writing in data for a culturing process by execution of OS (Operating System) and a culture program. The I/O 146 is used for taking in the input data from the input part 142, outputting displaying data to the display part 54, etc.

The storage part 148 is a recording medium for a program, data, etc. The storage part 148 includes a program storage part 150, a data storage part 152 and a RAM (Random-Access Memory) 154. The program storage part 150 is made by a recording medium. OS, firmware such as a culture program and a pressure and circulation culture control program, and various applications are stored in the program storage part 150. The RAM 154 is used for program processing.

The timer part 149 is an example of a time measuring means. The timer part 149 is used for measurement of elapsing time in pressure operation, time measurement for calculating pressure operation per unit time, etc.

Figure 8:
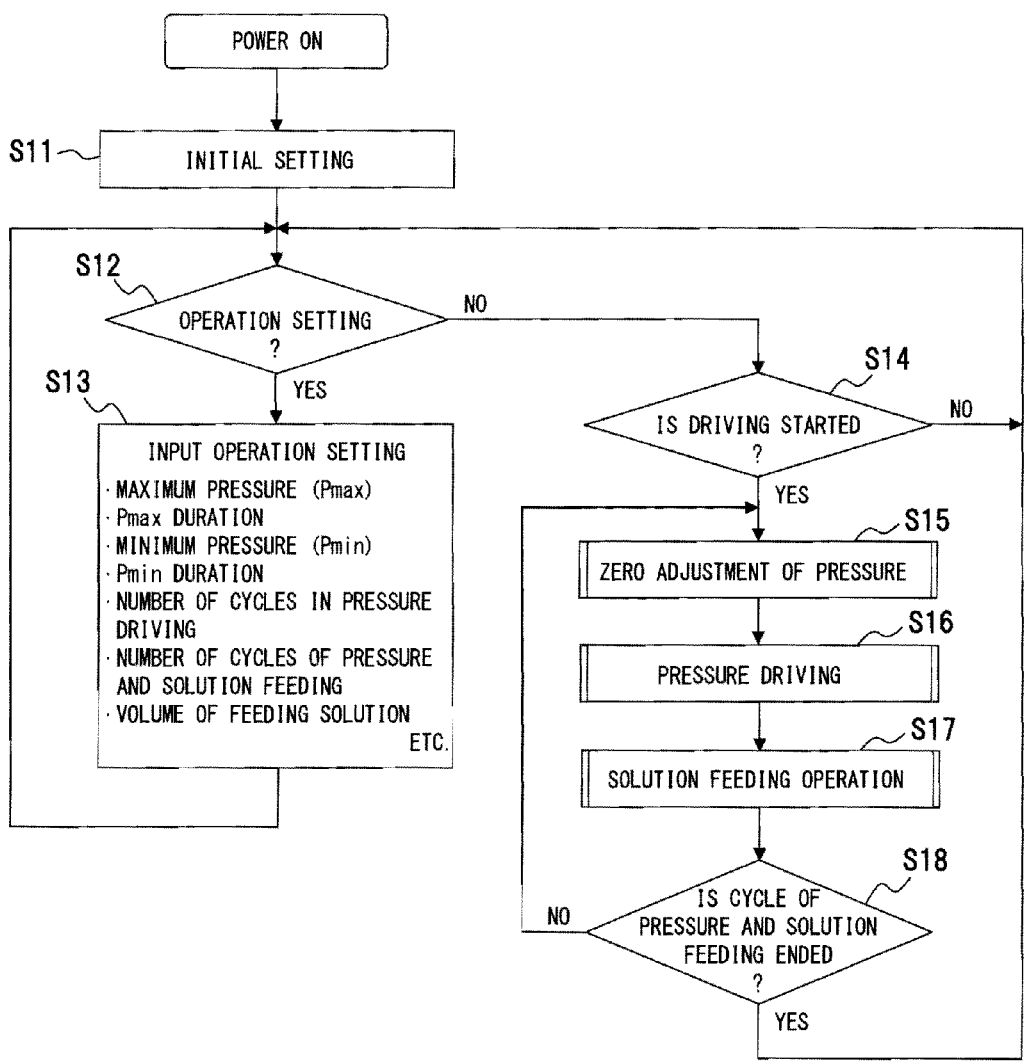
FIG. 8 is a flowchart depicting the procedure of a main routine.

A culturing process will be described with reference to FIG. 8. FIG. 8 is a flowchart depicting the procedure of a main routine.

As depicted in FIG. 8, an initial setting (step S11) is executed by turning power on in a main routine of this culturing process. In this initial setting, initialization of the I/O 146 of the control unit 120, setting of various initial values, etc. are executed.

After the completion of the initial setting, whether to execute operation setting or not is determined (step S12). In this operation setting, it is determined whether a mode of executing the operation setting is selected in the input part 142 or not. If the operation setting is executed (YES of step S12), modification of setting of various kinds can be executed (step S13). Setting items or modifiable items include setting such as the maximum pressure (Pmax), the maximum pressure duration (Pmax duration), the minimum pressure (Pmin), the minimum pressure duration (Pmin duration), the number of repeated sets of Pmax and Pmin in pressure driving (the number of cycles in pressure driving), the number of repeated series of pressure driving and solution feeding operation (the number of cycles of pressure and solution feeding), and the volume of feeding solution.

The maximum pressure (Pmax) is the highest pressure applied from the pressure generator unit 9 to the culture chamber part 7. The maximum pressure duration (Pmax duration) is duration of the maximum pressure. The minimum pressure (Pmin) is the lowest pressure applied from the pressure generator unit 9 to the culture chamber part 7. The minimum pressure duration (Pmin duration) is duration of the minimum pressure. The number of repeated sets of Pmax and Pmin in pressure driving (the number of cycles in pressure driving) indicates how many times a pressure changes in pressure driving. The number of repeated series of pressure driving and solution feeding operation (the number of cycles of pressure and solution feeding) indicates how many times of repeats per unit time. The volume of feeding solution is the volume of the culture solution 14 that is circulated through the culture chamber part 7 in one solution feeding operation.

After the completion of this operation setting, the procedure returns to step S12 to execute the determination of the operation setting again (step S12). If no operation setting is executed (NO of step S12), whether there are instructions to start driving is determined (step S14). If the input part 142 issues the instructions to start driving (YES of step S14), zero adjustment of a pressure is executed (step S15).

After the completion of the zero adjustment, the procedure moves to pressure driving (step S16), and solution feeding operation is executed (step S17). The pressure driving and solution feeding operation are executed alternately, and it is monitored whether the cycle of pressure and solution feeding is ended or not (step S18). The zero adjustment of a pressure may be executed in the middle of the cycle of pressure and solution feeding. In this step S18, it is determined whether the number of the cycles of pressure and solution feeding reaches the predetermined value or not. A set of pressure driving and solution feeding operation is continued until the number of the cycles thereof reaches the predetermined value. When the number of the cycles of pressure and medium feeding reaches the predetermined value (YES of step S18), the procedure returns to step S12. The end of the cycles of pressure and solution feeding may be by a user stopping driving instead of step S18.

Figure 9:
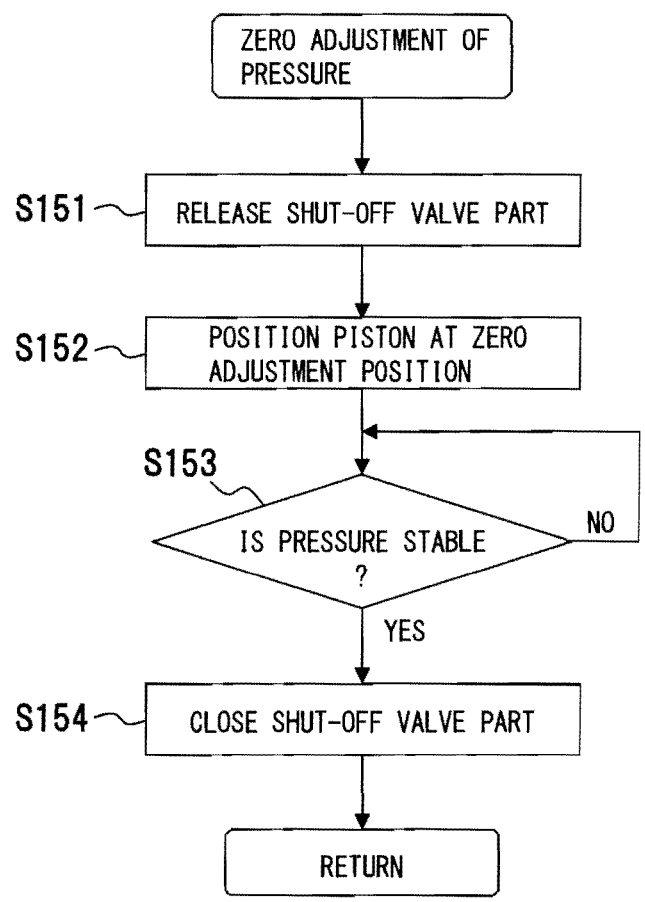
FIG. 9 is a flowchart depicting the procedure of zero adjustment of a pressure.
Figure 10:
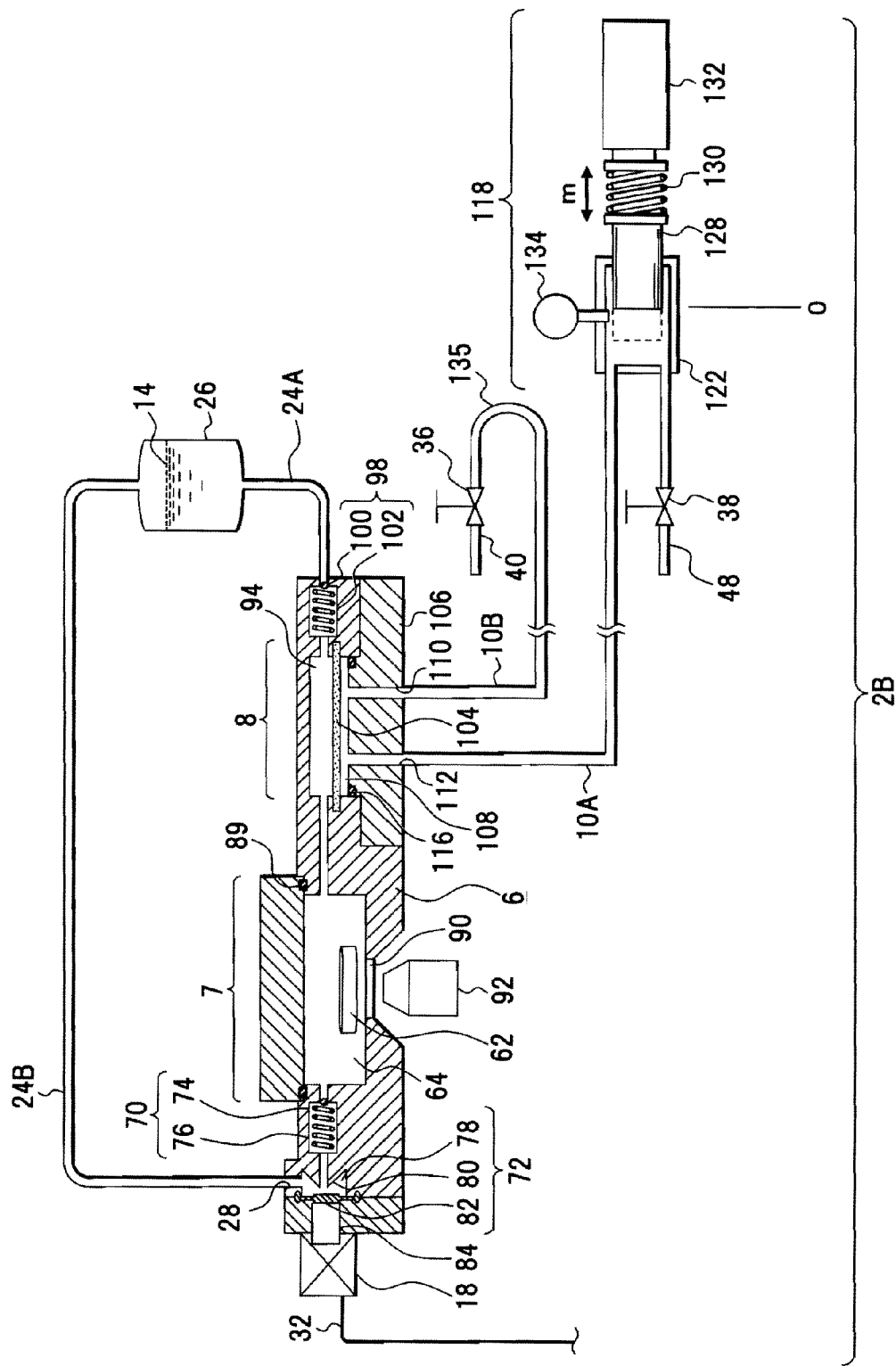
FIG. 10 depicts the operation of the zero adjustment of a pressure.

The zero adjustment of a pressure will be described with reference to FIGS. 9 and 10. FIG. 9 is a flowchart depicting the procedure of the zero adjustment of a pressure, and FIG. 10 depicts the operation of the zero adjustment.

This procedure is the procedure of step S15 of the main routine (FIG. 8). In this procedure, as depicted in FIG. 10, a pressure applied to the cultured object 62 under a released state of the shut-off valve part 72 is defined as a reference pressure Pref=0. Thus, the shut-off valve part 72 is released (step S151), and the pressure drive part 132 is driven so that the piston 128 is positioned at a zero adjustment position as the predetermined position (step S152). At this time, the pressure medium 34 in the pressure piping 10A and 10B may be adjusted by the syringe 44 so that the pressure transmission film 104 is flat or almost flat. Such adjustment is executed, and it is determined whether the value of the pressure sensor 134 is stable or not (step S153). If the pressure indicated by the pressure sensor 134 is stable (YES of step S153), the value of the pressure indicated by the pressure sensor 134 at this time is defined as the reference pressure Pref=0. This reference pressure is stored, the shut-off valve part 72 is closed (step S154), and the procedure returns to the main routine.

Figure 11:
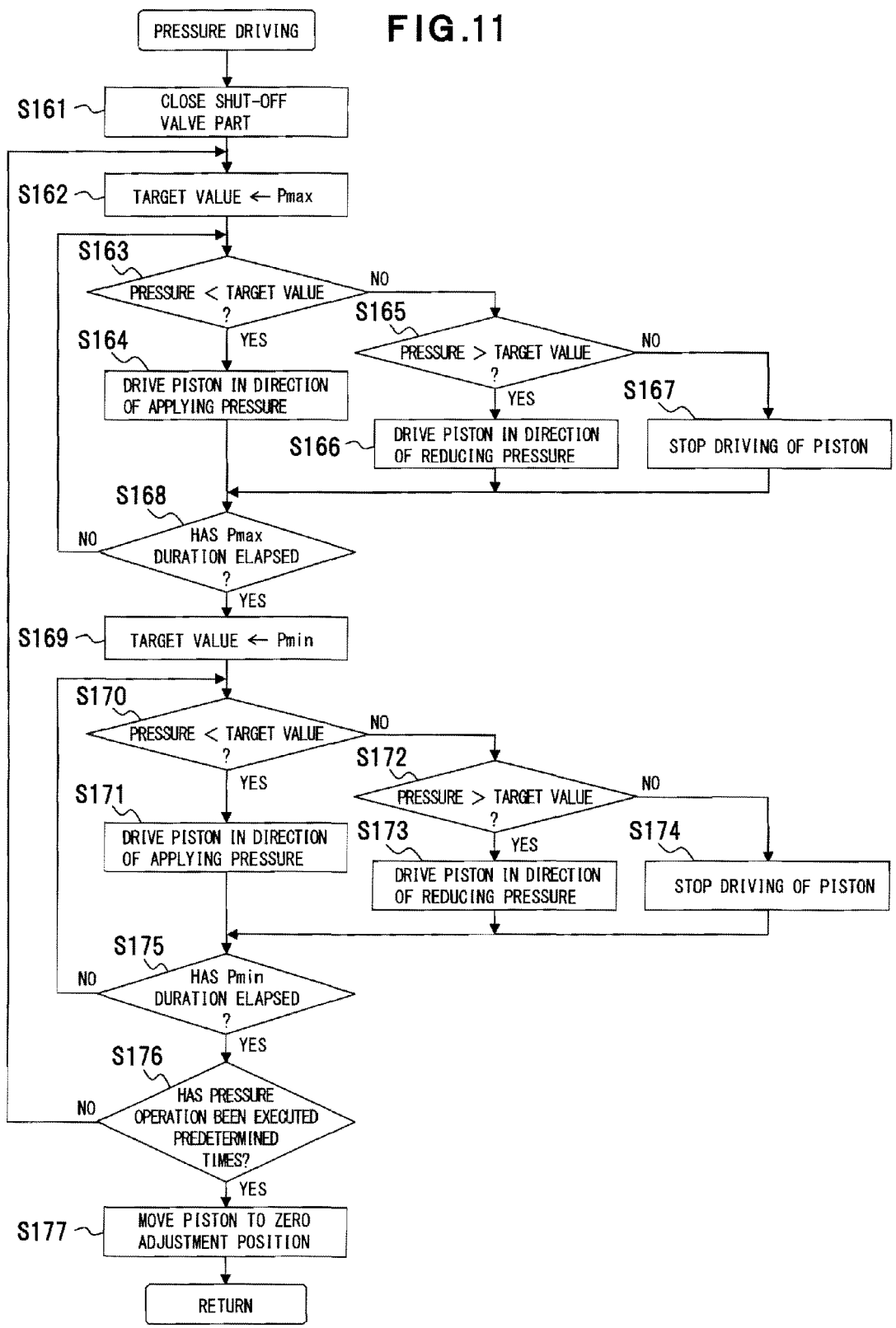
FIG. 11 is a flowchart depicting the procedure of pressure driving.
Figure 12:
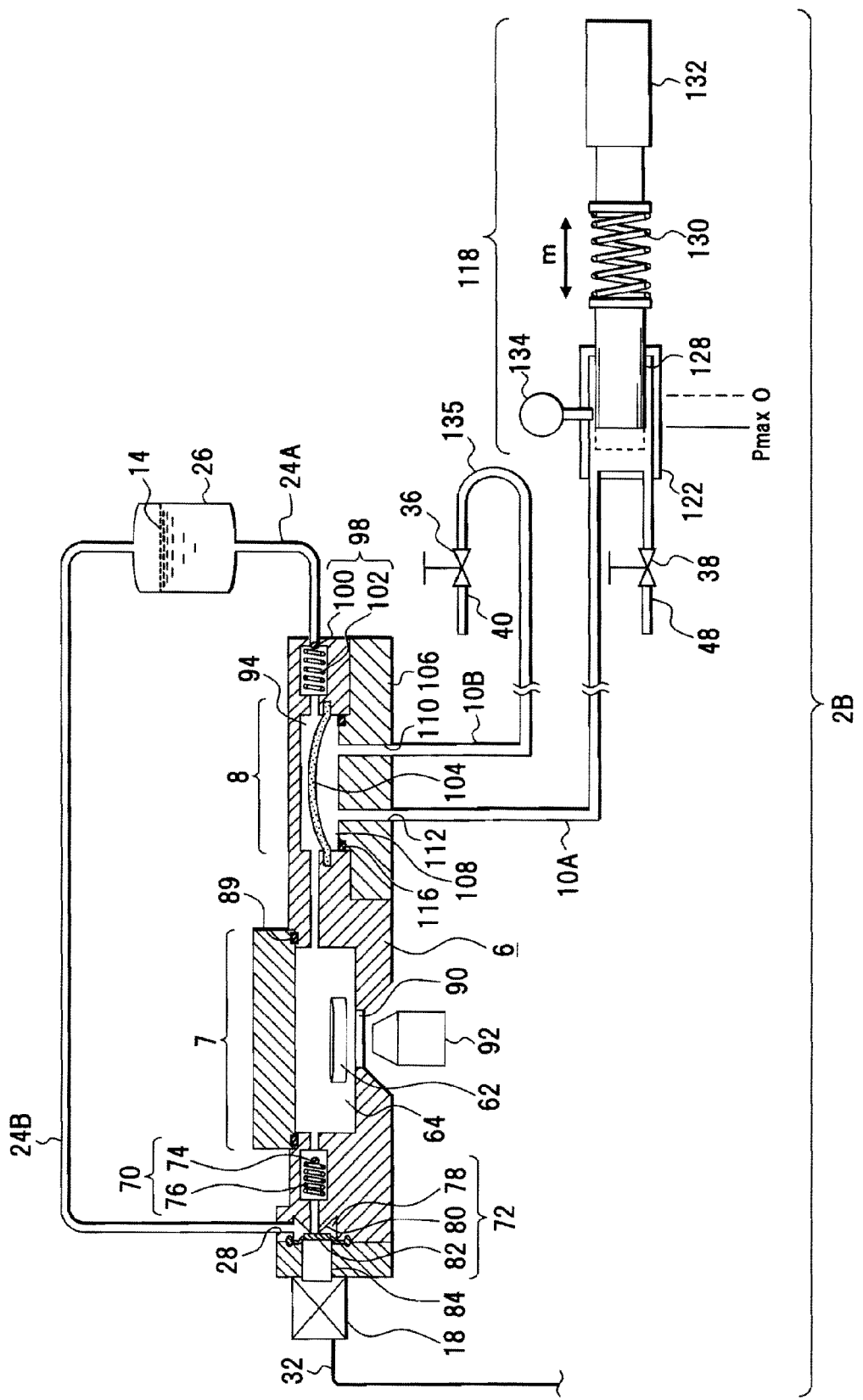
FIG. 12 depicts pressure driving operation.
Figure 13:
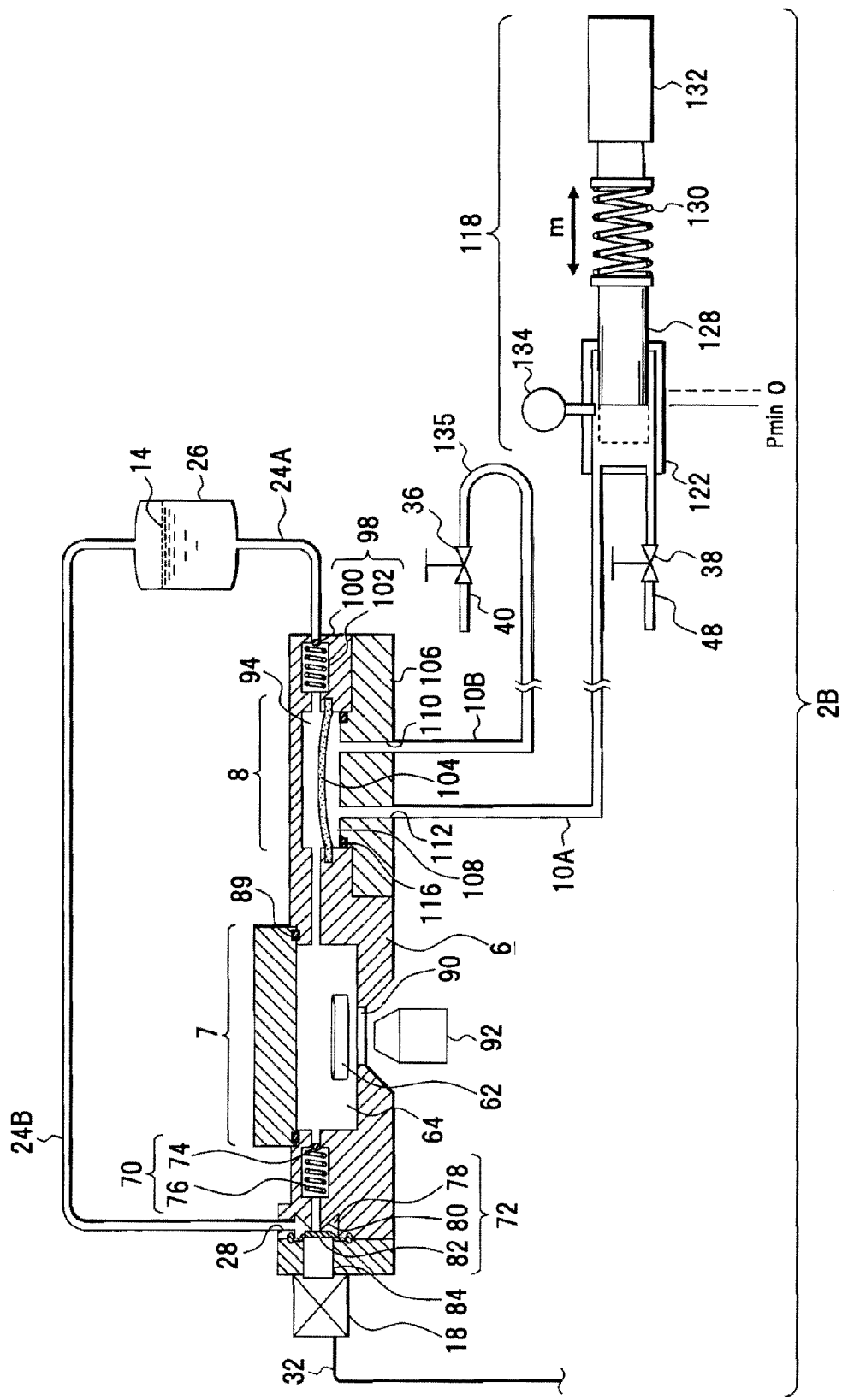
FIG. 13 depicts pressure driving operation.

The pressure driving will be described with reference to FIGS. 11, 12 and 13. FIG. 11 is a flowchart depicting the procedure of the pressure driving, FIG. 12 depicts the pressure operation in the maximum pressure, and FIG. 13 depicts the pressure operation in the minimum pressure.

This procedure is the procedure of step S16 of the main routine (FIG. 8). In this procedure of the pressure driving, as depicted in FIG. 12, the shut-off valve part 72 is closed (step S161), and the maximum pressure (Pmax) is set as a target value of a detected value by the pressure sensor 134 (step S162).

A pressure is monitored by the pressure sensor 134 after the pressure driving is started (step S163). If the detected value by the pressure sensor 134 is smaller than the maximum pressure (Pmax) that is the target value (YES of step S163), the piston 128 is driven by the pressure drive part 132 in the direction of applying a pressure (step S164).

If the detected value by the pressure sensor 134 is not smaller than the target value (Pmax) (NO of step S163), it is determined whether the detected value by the pressure sensor 134 is larger than the target value (step S165). If the detected value by the pressure sensor 134 is larger than the target value (YES of step S165), the piston 128 is driven by the pressure drive part 132 in the direction of reducing a pressure (step S166). If the detected value by the pressure sensor 134 is not larger than the target value (NO of step S165), the driving of the piston 128 is stopped by the pressure drive part 132 (step S167).

It is monitored whether the maximum pressure duration (Pmax duration) has elapsed (step S168), and the detected value by the pressure sensor 134 is controlled so as to be kept the maximum pressure (Pmax) (step S169).

If the maximum pressure duration (Pmax duration) has elapsed (YES of step S168), the minimum pressure (Pmin) is set for the target value of the detected value by the pressure sensor 134 (step S169).

After this minimum pressure is set, the pressure is monitored by the pressure sensor 134 (step S170). As depicted in FIG. 13, if the detected value by the pressure sensor 134 is smaller than the minimum pressure (Pmin) that is the target value (YES of step S170), the piston 128 is driven by the pressure drive part 132 in the direction of applying a pressure (step S171).

If the detected value by the pressure sensor 134 is not smaller than the target value (Pmin) (NO of step S170), it is determined whether the detected value by the pressure sensor 134 is larger than the target value (step S172). If the detected value by the pressure sensor 134 is larger than the target value (YES of step S172), the piston 128 is driven by the pressure drive part 132 in the direction of reducing a pressure (step S173). If the detected value by the pressure sensor 134 is not larger than the target value (NO of step S172), the driving of the piston 128 is stopped by the pressure drive part 132 (step S174).

It is monitored whether the minimum pressure duration (Pmin duration) has elapsed (step S175), and the detected value by the pressure sensor 134 is controlled so as to be kept the minimum pressure (Pmin) (step S175).

It is monitored whether the number of executions of the pressure operation reaches the predetermined value or not (step S176). That is, the pressure operation is repeated until the number of executions of the pressure operation reaches the number of repeated sets of Pmax and Pmin in the pressure driving (the number of cycles in pressure driving). If the number reaches the predetermined value (YES of step S176), the position of the piston 128 is moved to the position where the zero adjustment has been executed (step S177), and the procedure is ended.

In this embodiment, a pressure value is monitored every time when a pressure is applied and reduced. A pressure may be applied and reduced continuously and a pressure may be monitored periodically. A pressure applying method is not limited to the pattern of the above embodiment.

Figure 14:
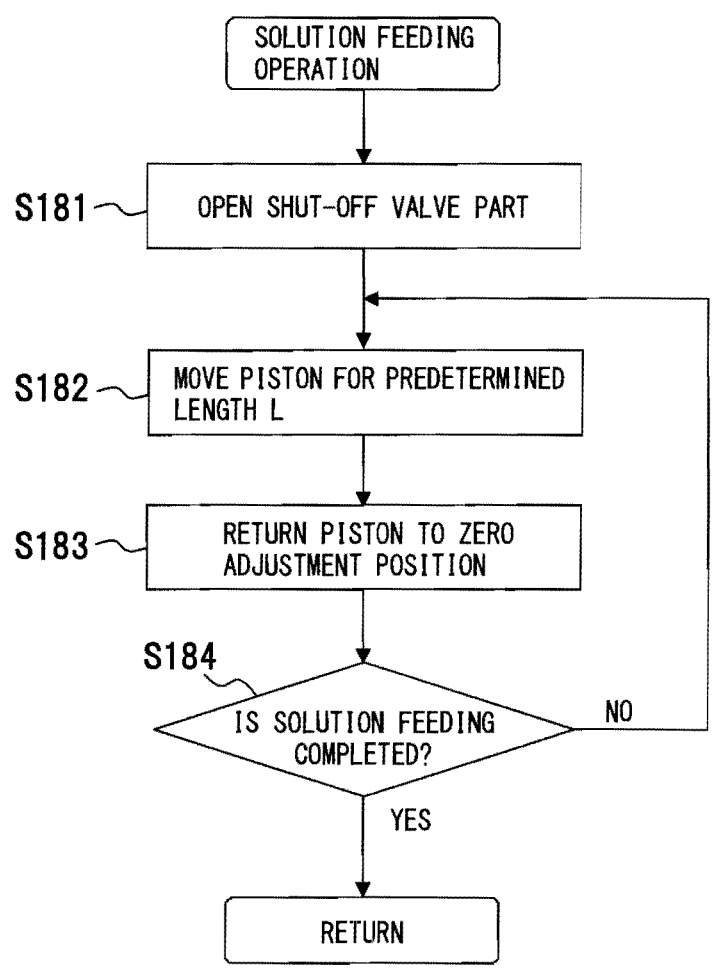
FIG. 14 is a flowchart depicting the procedure of a solution feeding process.
Figure 15:
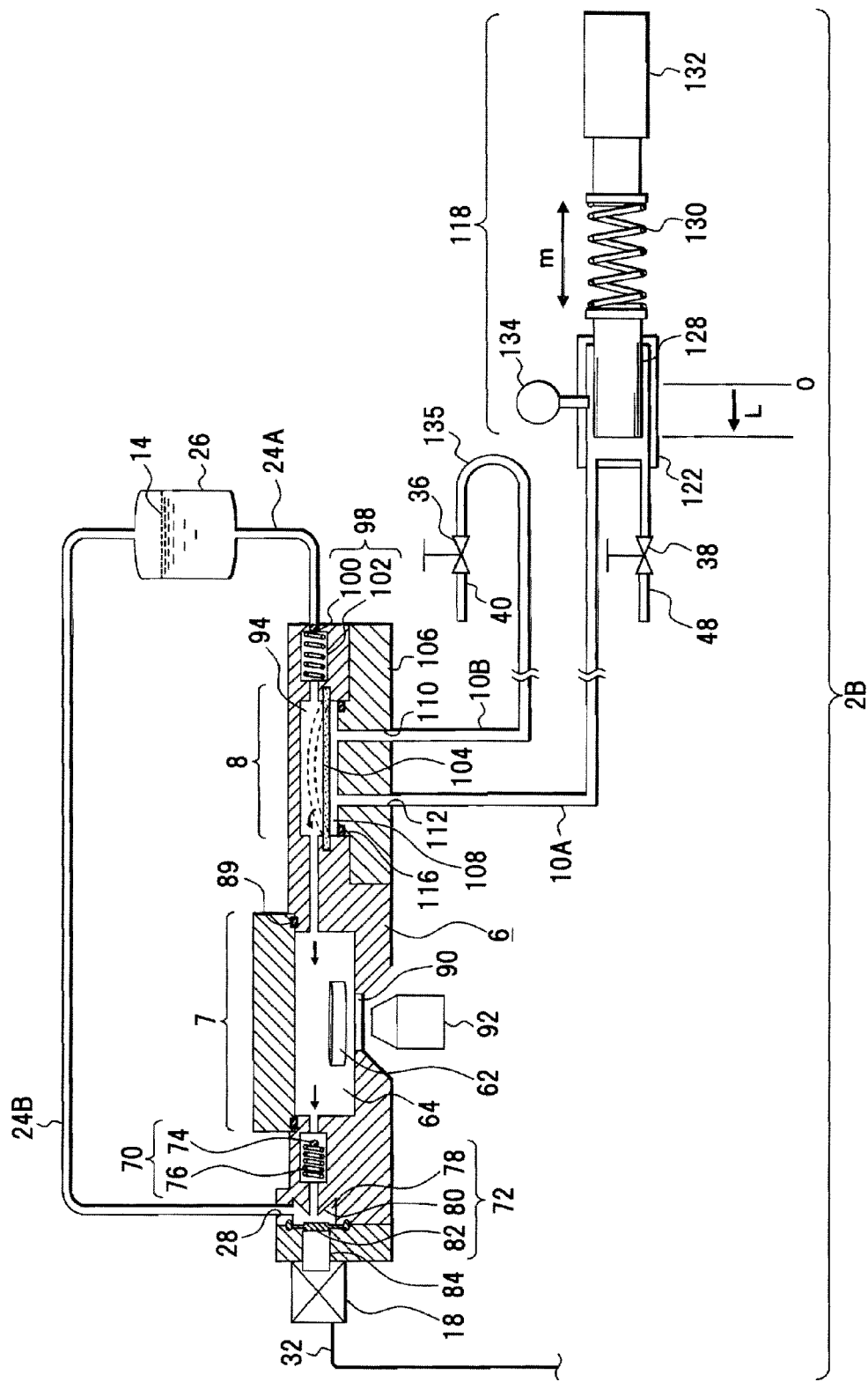
FIG. 15 depicts solution feeding operation.

The solution feeding operation will be described with reference to FIGS. 14, 15 and 16. FIG. 14 is a flowchart depicting the procedure of a solution feeding process, FIG. 15 depicts an extrusion state of the culture solution, and FIG. 16 depicts a suck state of the culture solution.

This procedure is the procedure of step S17 of the main routine (FIG. 8). In this solution feeding operation, feeding of the culture solution 14 is realized by application and reduction of a pressure to/from the culture circuit 30 that is for executing solution feeding, according to reciprocating operation of the piston 128 with the shut-off valve part 72 in an opened state. The reciprocating operation of the piston 128 is realized by the control that the piston 128 is plunged from the zero adjustment position of the piston for a predetermined length L, and returned to the zero adjustment position again. Thereby, the culture solution 14 is drawn into a holder and a pressure transmission part due to an external pressure with a first valve in a released state and a second valve in a shut-off state. The culture solution 14 is also made to flow out of a holder and a pressure transmission part due to an external pressure with a first valve in a shut-off state and a second valve in a released state.

In this procedure, as depicted in FIG. 14, the shut-off valve part 72 is kept an opened state (step S181), and reciprocation operation of the piston 128 is executed. In this reciprocation operation, as depicted in FIG. 15, the pressure medium 34 is extruded by the movement of the piston 128 for the predetermined length L (step S182). Thereby, the pressure transmission film 104 of the culture circuit 30 with the shut-off valve part 72 which is opened expands and protrudes to the pressure transmission space 94 side as depicted in a broken line. The culture solution 14 of the volume of this protrusion is extruded from the shut-off valve part 72. The culture solution 14 does not flow back due to the check valve 98 which is a first valve.

Figure 16:
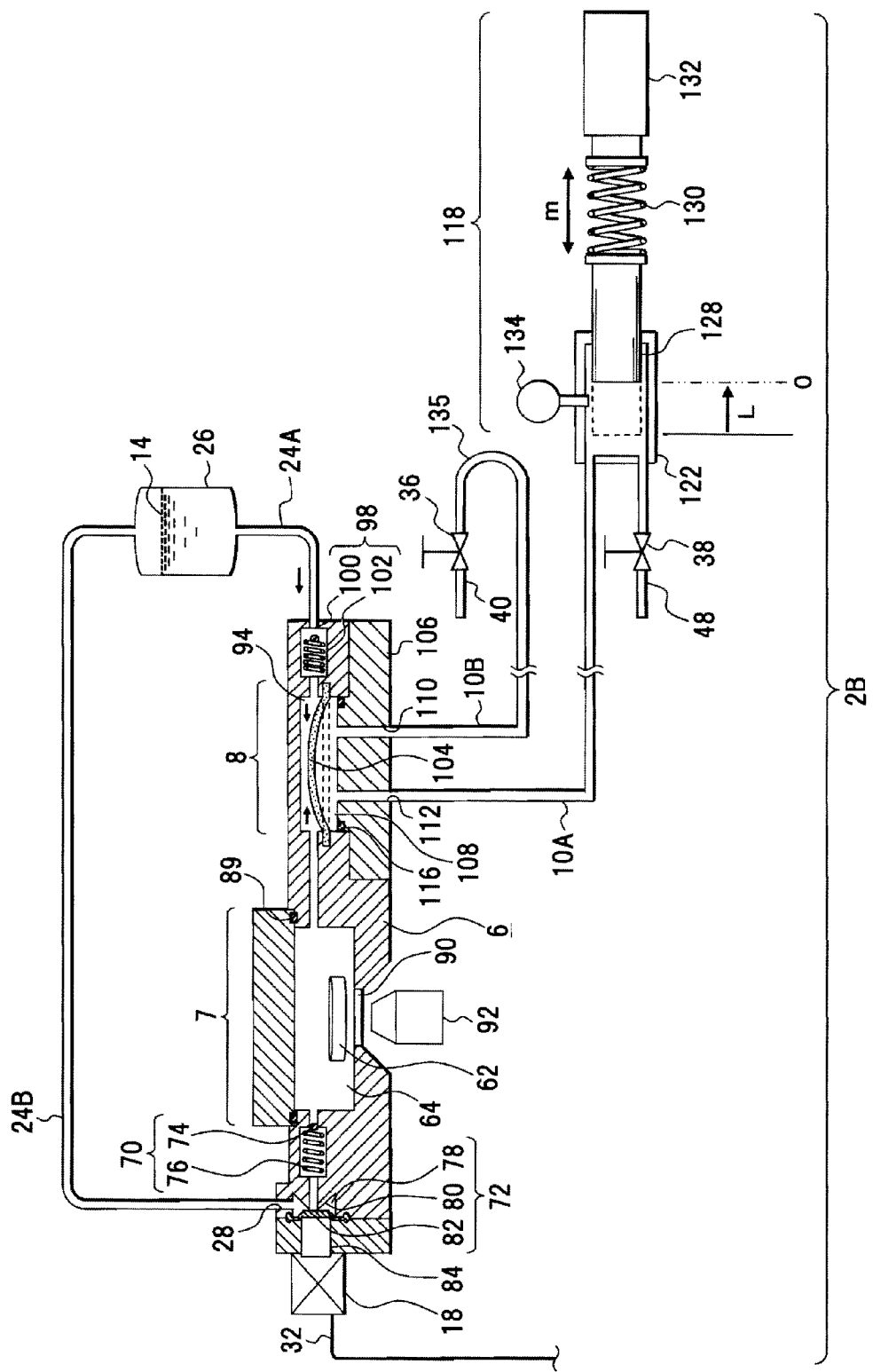
FIG. 16 depicts solution feeding operation.

As depicted in FIG. 16, if the piston 128 is returned to the zero adjustment position (step S183), the pressure transmission film 104 which has expanded to the pressure transmission space 94 is restored to the original position as depicted in a broken line. The culture solution 14 of the volume of the restoration enters into the pressure transmission space 94 from the check valve 98 side. In this case, the check valve 70 which is a second valve blocks the outflow of the culture solution 14. In case of no check valve 70 disposed, the shut-off valve part 72 may be closed.

The reciprocation movement of the piston 128 is repeated until the predetermined solution feeding is ended. It is determined whether the solution feeding of the predetermined volume is completed or not (step S184), and if the solution feeding of the predetermined volume is completed, the procedure is ended and returns to the main routine (FIG. 8).

The volume of feeding the culture solution 14 may be set in the input part 142 optionally, and may change according to the culture circuit 30.

Figure 17A:
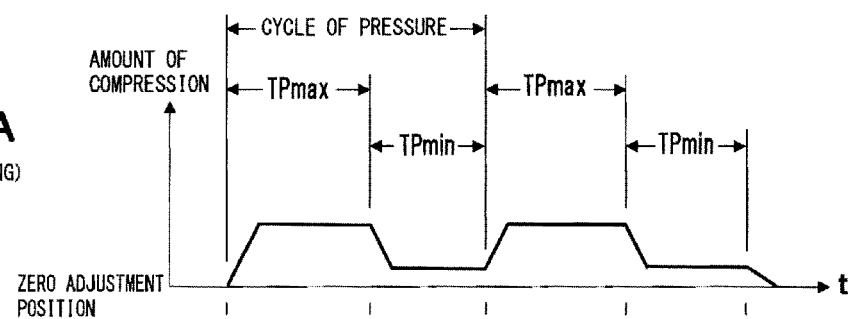
FIGS. 17A and 17B depict pressures corresponding to the reciprocation operation of a piston in the pressure driving.
Figure 17B:
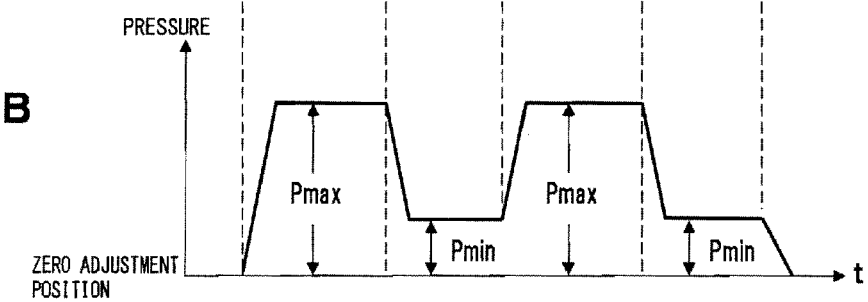

The pressure driving and solution feeding driving will be described with reference to FIGS. 17A, 17B, 18A and 18B. FIGS. 17A and 17B depict stretch of the spring and pressures in the pressure driving, and FIGS. 18A and 18B depict the reciprocation of the piston and pressures in the solution feeding driving.

As depicted in FIG. 17A, in the pressure driving, reciprocation movement is repeated such that: the piston 128 advances to the maximum pressure position from the zero adjustment position and the advance position is maintained for the predetermined period; the piston 128 then retreats from the maximum pressure position to the minimum pressure position after the predetermined period has elapsed and the retreat position is maintained for the predetermined period; and the piston 128 advances to the maximum pressure position from the minimum pressure position after the predetermined period has elapsed. By this reciprocation of the piston 128, as depicted in FIG. 17B, the maximum pressure and the minimum pressure alternately operate on the culture solution 14 through the pressure medium 34 such that: the pressure of the zero adjustment position or the minimum pressure (Pmin) shifts to the maximum pressure (Pmax); the maximum pressure (Pmax) is maintained and then dropped down to the minimum pressure (Pmin); and the minimum pressure (Pmin) is maintained for the predetermined period. This pressure change operates on the cultured object 62 through the culture solution 14. At this time, the fluctuation in the volume of the solution depending on the travel distance of the piston 128 arises. In FIGS. 17A and 17B, TPmax is the time period starting from the time point when the minimum pressure or the pressure at the zero adjustment position starts to rise to the maximum pressure, continuing for the duration of the maximum pressure, and ending at the time point when the maximum pressure starts to switch to the minimum pressure. TPmin is the time period starting from the time point when the maximum pressure starts to drop down to the minimum pressure, continuing for the duration of the minimum pressure, and ending at the time point when the minimum pressure starts to rise to the maximum pressure.

Figure 18A:
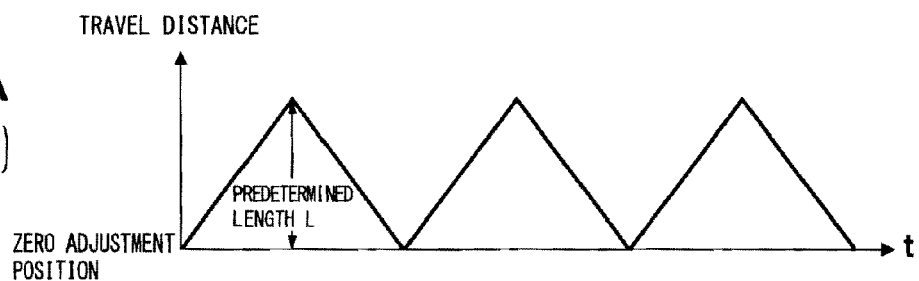
FIGS. 18A and 18B depict pressures corresponding to the reciprocation operation of the piston in solution feeding driving.
Figure 18B:
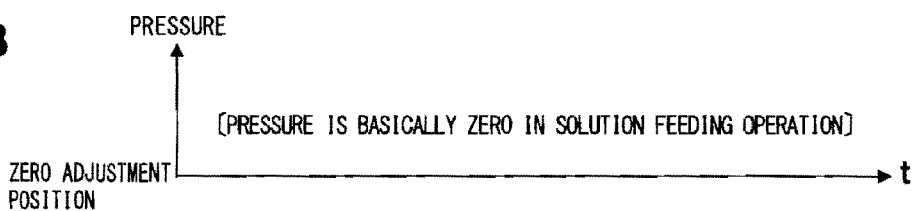

In the solution feeding driving, as depicted in FIG. 18A, the reciprocation movement that the position of the predetermined length L and the zero adjustment position alternately recur concerning the position of the piston 128 is performed. Since the shut-off valve part 72 is opened relative to this reciprocation of the piston 128, the pressure of the culture solution 14 is basically zero as depicted in FIG. 18B. The fluctuation of the volume due to back and forth movement of the pressure transmission film 104 relative to this reciprocation movement of the piston 128 generates extrusion and suck of the culture solution 14, and feeding of the culture solution 14 to the culture chamber part 7 arises.

Third Embodiment

A third embodiment discloses a structure of pressure piping different from the above embodiments. In the first and second embodiments, a plurality of sets of pressure piping 10A and 10B are used. However, single pressure piping 10A may be used.

Figure 19:
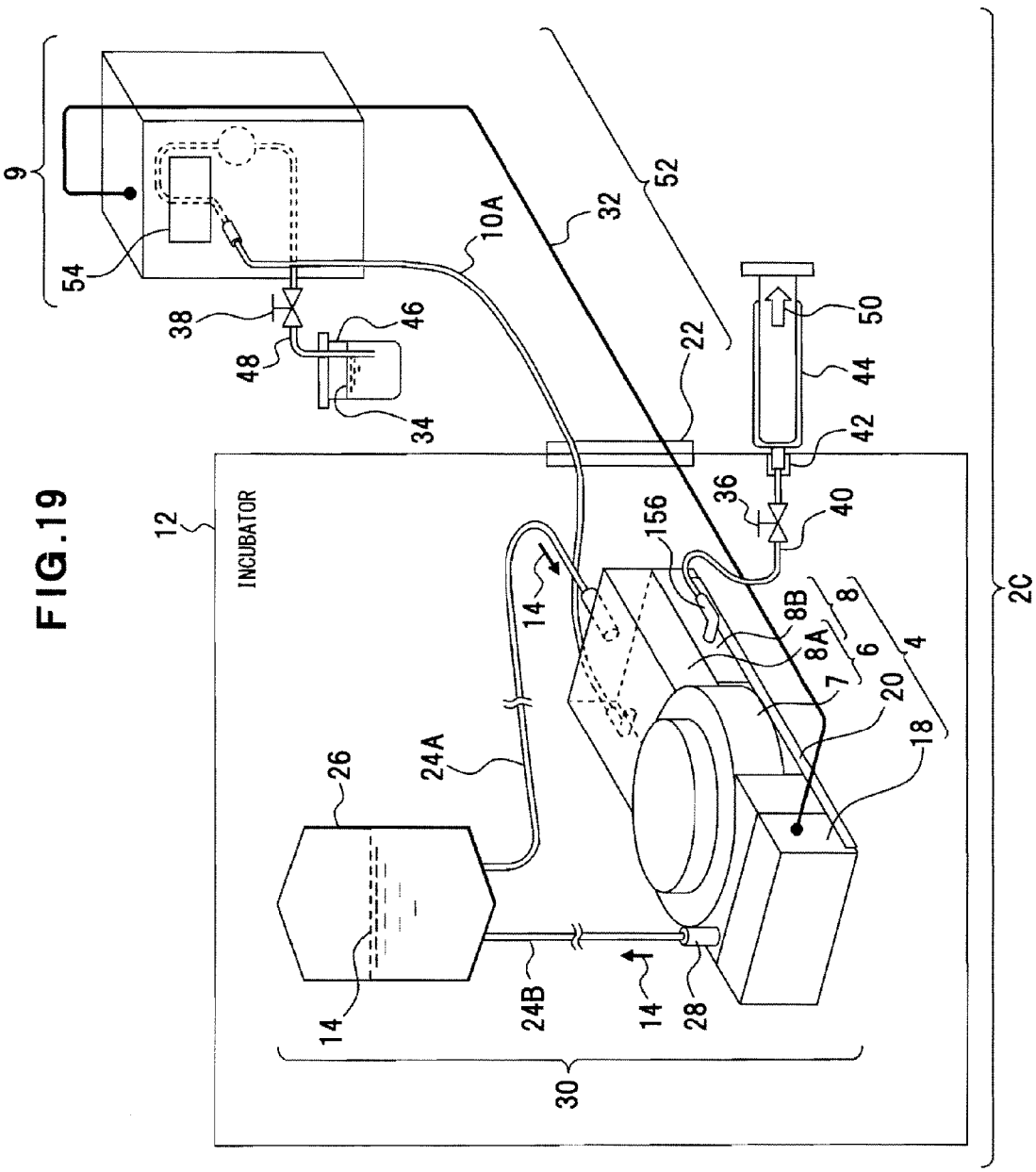
FIG. 19 depicts an example of a pressure and circulation culture apparatus according to a third embodiment.

This pressure and circulation culture apparatus 2C is formed as depicted in FIG. 19 such that: the culture unit 4 and the pressure generator unit 9 are coupled by the single pressure piping 10A; the syringe 44 is connected via the above described tube 40 to the port part 156, to which the pressure piping 10B is connected in the first and second embodiments; and the pressurized water block valve 36 is provided in the middle of the tube 40.

According to such a structure, the pressure operation and solution feeding operation can be executed as well as the above described embodiments. In FIG. 19, the same parts as those of FIG. 2 are denoted by the same reference numerals, and description thereof is omitted.

Fourth Embodiment

In a fourth embodiment, a plurality of pressure and circulation culture apparatuses are juxtaposed and a pressure and circulation culture system that allows multi culture is formed.

Figure 20:
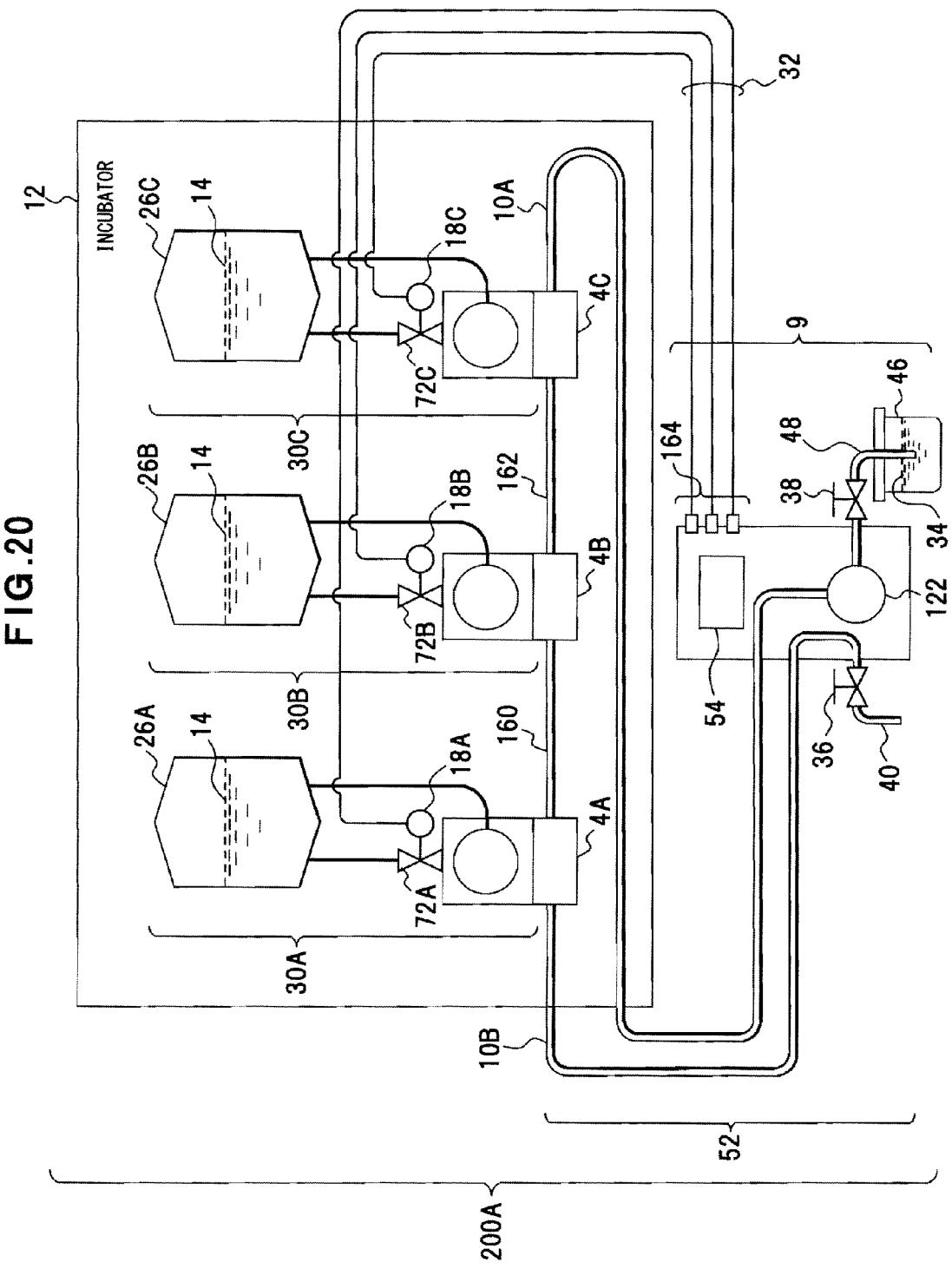
FIG. 20 depicts an example of a pressure and circulation culture system according to a fourth embodiment.

The fourth embodiment will be described with reference to FIG. 20. FIG. 20 depicts an example of a pressure and circulation culture system according to the fourth embodiment. In FIG. 20, the same parts as those of FIG. 2 are denoted by the same reference numerals.

In this pressure and circulation culture system 200A, culture circuits 30A, 30B and 30C are formed by three culture units 4A, 4B and 4C, respectively, as pressure and circulation culture apparatuses. The single pressure generator unit 9 can apply a pressure and feed solution to these culture circuits 30A to 30C.

The culture units 4A to 4C are arranged in series using piping 160 and 162. The pressure piping 10A is connected to the side of the culture unit 4A which is arranged in series, and the pressure piping 10B is connected to the side of the culture unit 4C which is arranged in series. The single pressure generator unit 9 applies a pressure and feeds solution.

In this case, a plurality of couples of the culture chamber part 7 and the pressure transmission part 8 can be connected to one pressure generator unit 9. The pressure circuit 52 having a plurality of culture units is formed by the tube 48 which is connected to a water supplying part of the pressure generator unit 9, the pressurized water block valve 38, the cylinder 122, the pressure piping 10A, three culture units 4A to 4C which are connected in series, the pressure piping 10B, the pressurized water block valve 36 of the drainage part of the pressure generator unit 9, and the tube 40. The culture chamber parts 7 form independent culture circuits 30A, 30B and 30C, respectively. The shut-off valve drive wirings 32 are connected to the shut-off valve drive units 18A, 18B and 18C (FIG. 6), respectively. The shut-off valve drive units 18A, 18B and 18C correspond to three output terminals 164 in the pressure generator unit 9, respectively. Thus, opening and closing the shut-off valve parts 72A, 72B and 72C may be executed individually. Since each culture circuit 30A to 30C is an independent circuit, cells, culture solution, a scaffold, growth factors, etc. can be distinguished to be cultured in each culture circuit 30A to 30C simultaneously. As to the strength and a pattern of a pressure, the same pressure can be applied in three circuits.

In circulation operation of the culture solution 14, the culture solution 14 may be made to flow to the culture circuits 30A, 30B and 30C one after another in order to avoid varying the volume of the culture solution 14 flowing in each circuit. A flow of the culture solution 14 for each culture circuit 30A, 30B and 30 is set in the control unit 120. Control according to the setting allows a different flow for each culture circuit 30A, 30B and 30C.

According to such a structure, a plurality of the culture chamber parts 7 are juxtaposed. Each culture chamber part 7 holds different cultured object 62 to allow each of the cultured object 62 to be cultured under a plurality of conditions simultaneously, and also allow each of the cultured object 62 to be cultured under the same condition. A main routine of a process (FIG. 8) is as described above.

Figure 21:
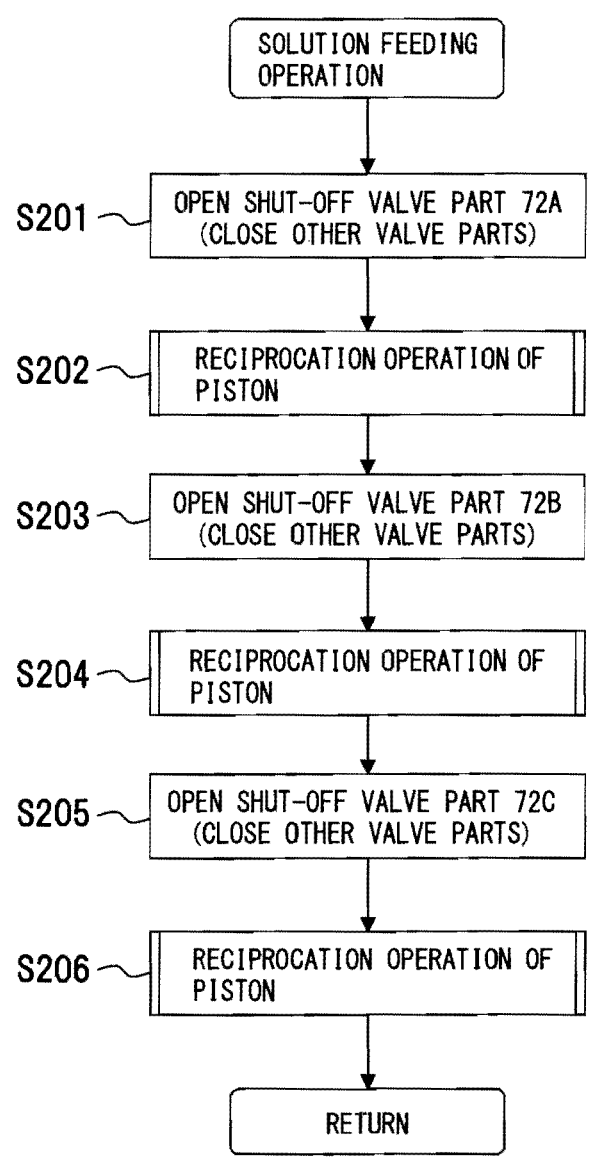
FIG. 21 is a flowchart depicting the procedure of a solution feeding process.

A solution feeding process of this pressure and circulation culture system 200A will be described with reference to FIG. 21. FIG. 21 is a flowchart depicting the procedure of the solution feeding process.

This procedure is the procedure in a case where the culture circuits 30A, 30B and 30C are provided as described above. In solution feeding of a plurality of the culture circuits 30A, 30B and 30C, an order is set for the culture circuits 30A, 30B and 30C, and solution feeding operation is executed. In any one of the culture circuits 30A, 30B and 30C, which is set as an object of the solution feeding, the reciprocation operation of the piston 128 is executed with any one of the shut-off valve parts 72A, 72B and 72C, which is an object of the solution feeding, in an opened state, and feeding of the culture solution 14 is executed. In this case, the reciprocation operation of the piston 128 is realized by the control that the piston 128 is plunged from the zero adjustment position of the piston 128 for the predetermined length L and returned to the zero adjustment position again.

In this procedure, if the feeding solution operation is executed in the order of the culture circuits 30A, 30B and 30C, the shut-off valve part 72A is opened, the other shut-off valve parts 72B and 72C are closed (step S201) and the reciprocation operation of the piston 128 is executed (step S202). Then, the shut-off valve part 72B is opened, the other shut-off valve parts 72C and 72A are closed (step S203) and the reciprocation operation of the piston 128 is executed (step S204). And then, the shut-off valve part 72C is opened, the other shut-off valve parts 72A and 72B are closed (step S205), the reciprocation operation of the piston 128 is executed (step S206), and the procedure returns to the main routine (FIG. 8).

Figure 22:
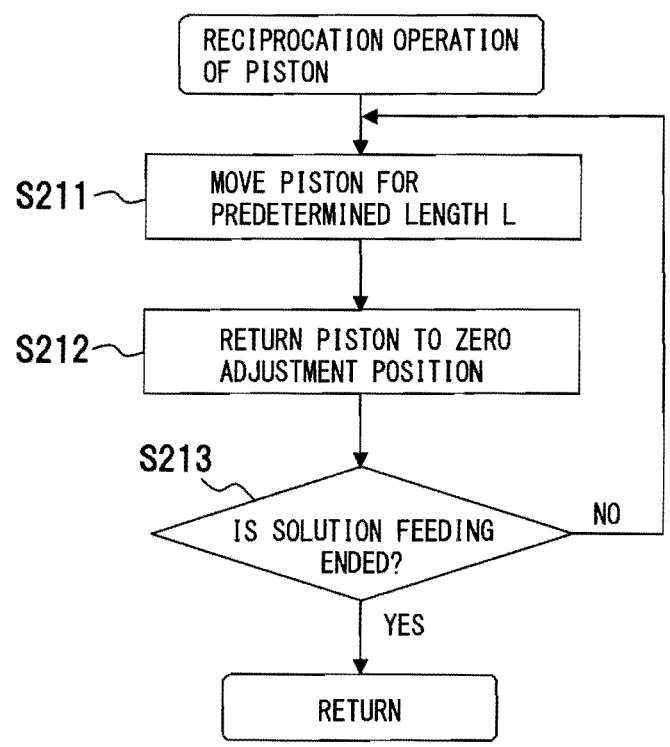
FIG. 22 is a flowchart depicting the procedure of reciprocation operation of a piston.

In this procedure, in the reciprocation operation of the piston 128, as depicted in FIG. 22, if the piston 128 is moved for the predetermined length L (step S211), the pressure medium 34 is extruded, and the pressure transmission film 104 of the culture circuit 30A where the shut-off valve part 72A is open is expanded to the pressure transmission space 94 for the same volume as the extrusion of the pressure medium 34. Thereby, the culture solution 14 is extruded from the shut-off valve part 72A. The check valve 98 blocks the backflow of the culture solution 14. If the piston 128 is returned to the zero adjustment position (step S212), the pressure transmission film 104 that expands to the pressure transmission space 94 side is returned to the original position, and the culture solution 14 advances from the check valve 98 side to the pressure transmission space 94 for the same volume as the return of the pressure transmission film 104. Since the check valve 70 is at the shut-off valve part 72A side, the culture solution 14 does not flow out. This reciprocation movement is repeated until the predetermined solution feeding is ended (step S213), and the culture solution 14 of the predetermined volume is fed.

This solution feeding by the reciprocation operation of the piston 128 is described relative to the shut-off valve part 72A. The description is also applied to the culture circuit 30B at the shut-off valve part 72B side and the culture circuit 30C at the shut-off valve part 72C side.

Fifth Embodiment

A fifth embodiment discloses a different structure of pressure piping. In the fourth embodiment, a plurality of sets of the pressure piping 10A and 10B are used. However, single pressure piping 10A may be used.

Figure 23:
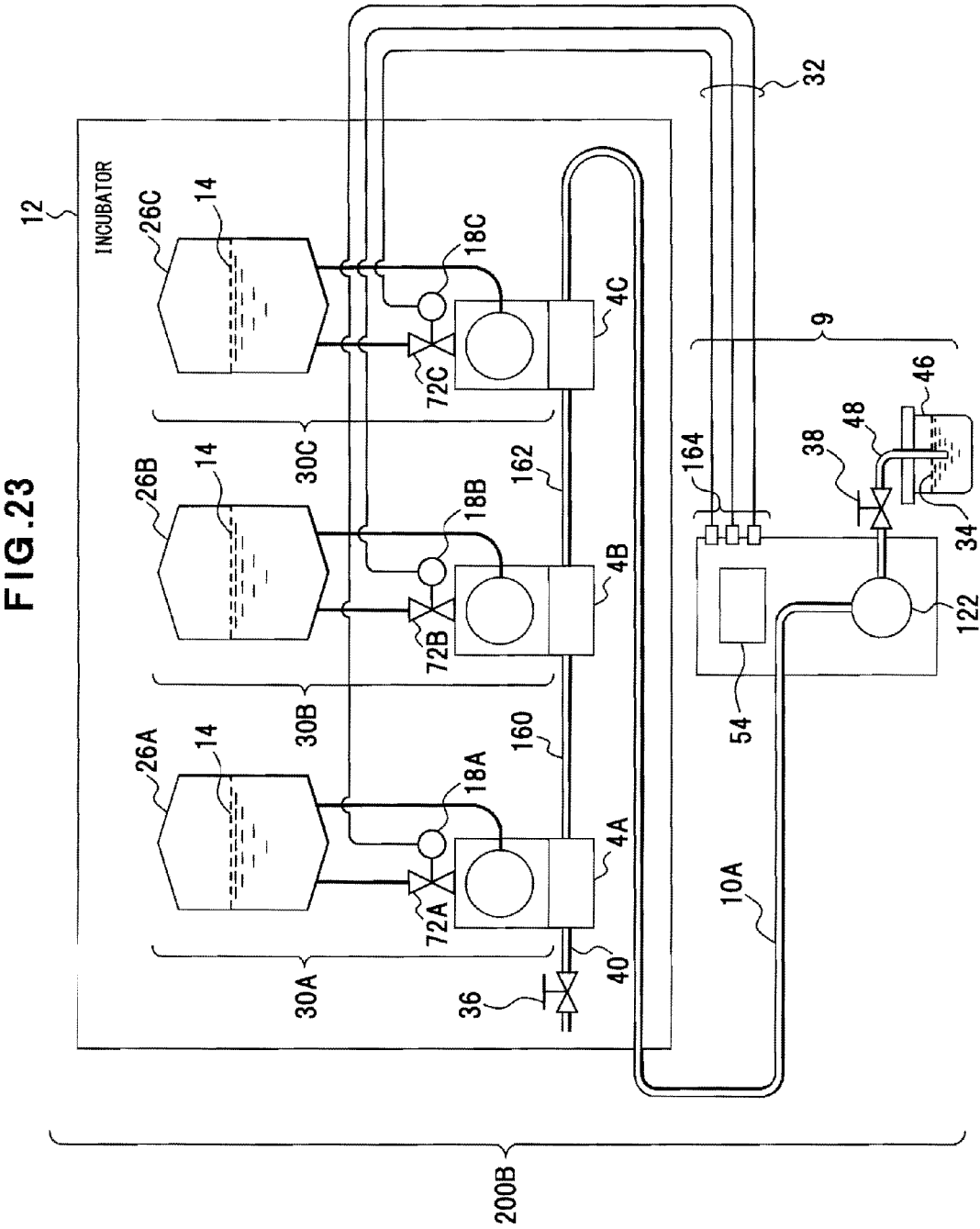
FIG. 23 depicts an example of a pressure and circulation culture system according to a fifth embodiment.

This pressure and circulation culture system 200B may be formed as depicted in FIG. 23 such that: the culture unit 4 and the pressure generator unit 9 are coupled by the single pressure piping 10A; the syringe 44 is connected via the above described tube 40 to the port part 156, to which the pressure piping 10B is connected in the fourth embodiment; and the pressurized water block valve 36 is provided in the middle of the tube 40, as well as the third embodiment (FIG. 19).

According to such a structure, the pressure operation and solution feeding operation can be executed as well as the above described embodiments. In FIG. 23, the same parts as those of FIG. 2 are denoted by the same reference numerals, and description thereof is omitted.

Features of Above Embodiments, and Other Embodiments (1) The culture unit 4 and the pressure generator unit 9 can be separated while hermeticity of the culture unit 4 is kept.

(2) Opening and closing the shut-off valve part 72 (72A, 72B and 72C) and pressure operation of the pressure generator unit 9 allows the culture solution 14 to apply a pressure to the cultured object 62, and allows feeding the culture solution 14.

(3) Driving control of the culture unit 4 and the pressure generator unit 9 can be executed in one place.

(4) Since the structure is simplified compared with the conventional apparatus, handleability is more improved and the cost of an apparatus itself can be reduced.

(5) Connection of a plurality of culture units is allowed, and the same pressure operation can be executed to each culture unit.

(6) The existing incubator can be utilized to establish setting of an environment such as temperature and gas concentration.

(7) In an experiment dealing with cells etc., there is the possibility that reproducibility can not be taken if start time etc. of each experiment are different although the same cells are used. Even in such a case, a culture experiment can be performed by setting of various conditions in one time, and thus a result of high reliability can be obtained. Therefore, the number of experiments can be reduced, and the reduction of the cost of culture can be achieved. That is, a comparison experiment, comparison of culture experiments for plural kinds of cells, etc. can be executed in one culture system simultaneously.

(8) A plurality of culture systems can be cultured simultaneously. Only the culture circuit 30 has to be kept axenic when a plurality of pieces of culture are executed simultaneously. The culture circuit 30 can be separated from the pressure circuit 52 which does not need to be axenic, and the structure needed is simple.

(9) The pressure transmission space 94 is adjacent to the holding space 64 of the cultured object 62 and is partitioned by the flexible film-formed pressure transmission film 104. A pressure transmission part is connected to the outside of the pressure transmission film 104. The pressure medium space 108 of a small volume is formed. These are disposed in the culture unit main body 6 to achieve simplification of the structure thereof.

(10) A hermetic circuit of a closed system is formed, high safety is achieved, and thus high cleanliness is not required for circumstances in culture. Simple culture of high accuracy can be realized.

(11) The culture unit main body 6 may be taken out of the incubator 12 to be inspected through a microscope. Alternatively, the incubator 12 can be inspected remotely by a microscope inserted thereinto. Since the culture system is a closed system, vaporization of the culture solution 14 is a small volume, and it is no matter for the culture system not to be humidified for a short period. Thus, no adverse effect is taken to a microscope.

(12) The culture unit main body 6 forms the culture circuit 30, and is coupled with the pressure transmission part 8. The pressure transmission film 104 is a flexible film, and divides the pressure medium 34 and the culture solution 14. Since a pressure is transmitted with almost no resistance, the efficiency of pressure transmission is well, and a pressure is not lost so much.

(13) Culture in a plurality of the culture unit main bodies 6 (child devices) can be performed by one pressure generator unit 9 (parent device). Open and close of the shut-off valve part 72 can switch between pressure application and circulation of culture solution, and thus, one device is allowed to play two roles which are pressure application and circulation.

(14) Since piping and a wiring can pass through a mating line of the main body and the door of the incubator 12, it is easy to dispose the culture unit 4 in the incubator 12. Moreover, sealing is processed for the penetration part 22 when the culture unit 4 is disposed in the incubator 12, and thus, airtightness of the incubator 12 can be kept.

(15) The range of a pressure can be selected by the spring 130 and the pressure sensor 134 which are used, and it is easily executed to switch a pressure between high and low.

(16) Opening the shut-off valve part 72 releases an interior pressure into the atmosphere. The pressure sensor 134 can be calibrated based on this pressure. In this case, a relative pressure of the pressure sensor 134 is calibrated to "0" (atmosphere). The inside of the culture chamber part 7 that is equal to the atmosphere can be controlled as a pressure "0" even if the depth of the culture solution reservoir 26 changes, or even if the pressure transmission film 104 receives tension.

(17) A pressure is checked every certain time. If a pressure is not adjustable, an alarm may be issued.

(18) If a plurality of the culture circuits 30 are used, solution feeding may be executed in every circuit in order. That is, solution feeding may be executed in a plurality of circuits one by one for every sequence. Alternatively, solution feeding may be executed in every circuit according to a sequence of the solution feeding.

(19) The culture solution 14 is interchanged after solution feeding. If a pressure is also calibrated at this time, a pressure application experiment can be executed under a correct pressure any time.

(20) While the culture chamber part 7 and the culture circuit 30 are secure because a closed system is kept, clean environment may be held therefor only when the cultured object 62 is taken out.

Figure 24:
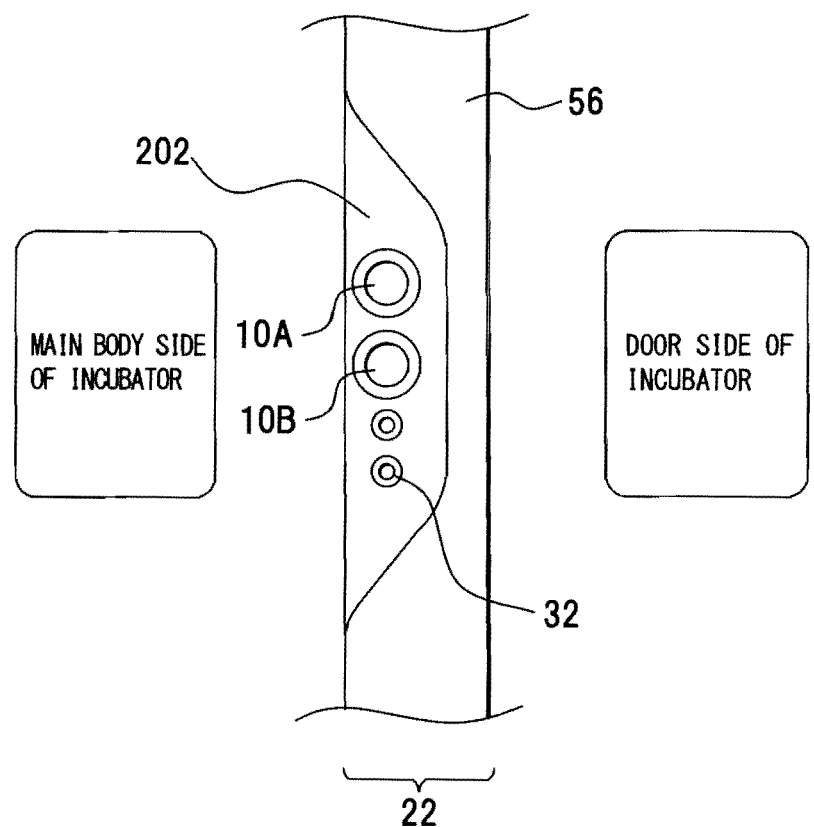
FIG. 24 depicts an example of a sealing portion disposed in a penetration part of an incubator.

(21) In the above embodiments, the penetration part 22 is illustrated in FIG. 3. For enforcing the sealing of the door packing 56 more, a sealing part 202 may be disposed, and the pressure piping 10A and 10B, and the shut-off valve drive wiring 32 may be penetrated through the sealing part 202 as depicted in FIG. 24.

According to the pressure and circulation culture apparatus of the present invention, any of the following effects can be obtained.

(1) A simplified mechanism can realize pressure on and circulation of culture solution which is supplied to a cultured object. A structure for the apparatus is simplified, the easy use of the apparatus is achieved, and the cost of the apparatus can be reduced.

(2) The apparatuses can be juxtaposed as a plurality of holders. Common pressure operation for a plurality of cultured objects can be performed through culture solution. Culture solution for a cultured object can be circulated through every holder.

According to the pressure and circulation culture system of the present invention, in addition to the above effects: a plurality of holders are connected and common pressure operation for a plurality of cultured objects can be performed through culture solution; culture solution for a cultured object can be circulated through every holder; and the system can be provided for multiple culture of cultured objects, production of cultures by multiple culture, and experimental culture for comparison.

While the detailed description of the invention has been described hereinabove, the present invention is not limited to the above description, and it is a matter of course that various variations and modifications can be made by those skilled in the art based on the spirit of the invention within the claims or disclosed herein, and needless to say, such variations and modifications are also encompassed in the scope of the present invention.

The pressure and circulation culture apparatus and the pressure and circulation culture system of this invention can realize pressure stimulation to a cultured object and feeding of culture solution with a simplified structure. Moreover, the pressure and circulation culture apparatus and the pressure and circulation culture system of this invention can be widely utilized for a high-accurate culture experiment and tissue culture, and thus are useful.

What is claimed is:

1. A pressure and circulation culture apparatus for culturing a cultured object, and for applying a pressure to a culture solution and releasing the pressure on the culture solution, the pressure and circulation culture apparatus comprising:
    an incubator in which a culture environment of the cultured object is maintained;
    a pressure generator unit that is outside the incubator; and
    a culture unit including a culture unit main body disposed inside the incubator;
    wherein the culture unit main body is separable from the culture unit, the culture unit main body culturing the cultured object with the culture unit, and
    wherein the culture unit main body comprises:
    a culture solution reservoir that reserves the culture solution;
    a culture solution circuit that circulates the culture solution from the culture solution reservoir through the culture unit main body;
    a holder that holds the cultured object, and the culture solution that circulates through the culture solution circuit;
    a pressure transmission part that is in fluid communication with the holder and transmits an external pressure to the culture solution in the holder, wherein the pressure generator unit is connected to the pressure transmission part via a pressure circuit that transmits the external pressure from the pressure generator unit to the pressure transmission part;
    a first valve that is disposed at an upstream side of the pressure transmission part, the first valve being in a closed position when a pressure in the pressure transmission part is higher than a predetermined pressure, the closed position of the first valve checking a backflow of the culture solution from the pressure transmission part to the culture solution circuit;
    a second valve that is disposed at a downstream side of the holder, the second valve being in a closed position when a pressure in the holder is lower than the predetermined pressure, and the second valve checking a backflow of the culture solution from the culture solution circuit to the holder while the culture solution is drawn into the holder; and
    a shut-off valve part that is disposed in the culture solution circuit at a downstream side of the holder and the second valve, the shut-off valve part being switched to a closed position during a process of applying the pressure to the holder, so as to check a circulation of the culture solution, and the shut-off valve part being switched to an open position during a process of circulating the culture solution,
    wherein the pressure and circulation culture apparatus further comprises:
    a shut-off valve drive unit that attaches to the shut-off valve part, the shut-off valve drive unit opening or closing the shut-off valve part;
    a pressure sensor that detects the pressure in the holder, the pressure being applied to the culture solution; and
    a processor that is programmed to execute each of the process of applying the pressure and the process of circulating the culture solution, wherein in the process of applying the pressure, the processor is programmed such that the pressure generator unit provides a pressure in the holder that alternates between at least a first target pressure and a second target pressure, the second target pressure being different from the first target pressure, and wherein in the process of circulating the culture solution, the culture solution is made to flow out of the holder after the process of applying the pressure, and then drawn into the holder after flowing out of the holder,
    wherein in the process of applying the pressure, the shut-off valve part is closed by the shut-off valve drive unit receiving a control output generated by the processor and the external pressure is applied from the pressure generator unit via the pressure circuit through the pressure transmission part to the holder, so that the pressure in the holder alternates between a first pressurization in which the pressure in the holder reaches and maintains the first target pressure and a second pressurization in which the pressure in the holder reaches and maintains the second target pressure,
    wherein after alternating between the first pressurization and the second pressurization, the process of applying the pressure moves to the process of circulating the culture solution,
    wherein in the process of circulating the culture solution, the shut-off valve part is released by the shut-off valve drive unit receiving the control output generated by the processor, and wherein in a process of making the culture solution flow out of the holder during the process of circulating the culture solution, the external pressure is applied from the pressure generator unit via the pressure circuit through the pressure transmission part to the culture solution in the holder with the first valve in a closed state and the second valve in an open state for making the culture solution in the holder flow into a downstream side of the culture solution circuit,
    wherein in a process of drawing the culture solution into the holder during the process of circulating the culture solution, the external pressure, which is applied from the pressure generator unit via the pressure circuit through the pressure transmission part to the holder, is reduced with the first valve in an open state and the second valve in a closed state, so as to draw the culture solution from a culture solution reservoir side into the holder,
    wherein the culture unit main body of the pressure and circulation culture apparatus is separable from the culture unit at the shut-off valve part and the pressure transmission part, and
    wherein the cultured object is transportable as a unit with the culture unit main body by making the culture unit main body separate from the culture unit at the shut-off valve part and the pressure transmission part after culture of the cultured object.

2. The pressure and circulation culture apparatus of claim 1,
    wherein a pressure transmission space that stores the culture solution is formed in the pressure transmission part,
    wherein the pressure transmission part comprises an external pressure operation part which applies the external pressure on a pressure transmission film that is disposed between the pressure transmission space and the external pressure operation part, and wherein the pressure transmission film is reciprocated by applying and reducing the external pressure, and the external pressure is transmitted to the culture solution.

3. A pressure and circulation culture system for culturing a cultured object, and for applying a pressure to a culture solution and releasing the pressure on the culture solution, the pressure and circulation culture apparatus comprising:

an incubator in which a culture environment of the cultured object is maintained;

a pressure generator unit that is outside the incubator; and a plurality of culture units disposed inside the incubator, each of the plurality of culture units comprising a culture unit main body:

wherein the culture unit main body is separable from the culture unit, the culture unit main body culturing the cultured object with the culture unit, and wherein the culture unit main body comprises:

a culture solution reservoir that reserves the culture solution;

a culture solution circuit that circulates the culture solution from the culture solution reservoir through the culture unit main body;

a holder that holds the cultured object, and the culture solution that circulates through the culture solution circuit;

a pressure transmission part that is in fluid communication with the holder and transmits an external pressure to the culture solution in the holder, wherein the pressure generator unit is connected to the pressure transmission part via a pressure circuit that transmits the external pressure from the pressure generator unit to the pressure transmission part;

a first valve that is disposed at an upstream side of the pressure transmission part, the first valve being in a closed position when a pressure in the pressure transmission part is higher than a predetermined pressure, the closed position of the first valve checking a backflow of the culture solution from the transmission part to the culture solution circuit;

a second valve that is disposed at a downstream side of the holder, the second valve being in a closed position when a pressure in the holder is lower than the predetermined pressure, and the second valve checking a backflow of the culture solution from the culture solution circuit to the holder while the culture solution is drawn into the holder; and a shut-off valve part that is disposed in the culture solution circuit at a downstream side of the holder and the second valve, the shutoff valve part being switched to a closed position during a process of applying the pressure to the holder, so as to check a circulation of the culture solution, and the shut-off valve part being switched to an open position during a process of circulating the culture solution, wherein the pressure and circulation culture system further comprises:

a shut-off valve drive unit that attaches to the shut-off valve part, the shut-off valve drive unit opening or closing the shut-off valve part:

a pressure sensor that detects the pressure in the holder, the pressure being applied to the culture solution; and a processor that is programmed to execute each of the process of applying the pressure and the process of circulating the culture solution, wherein in the process of applying the pressure, the processor is programmed such that the pressure generator unit provides a pressure in the holder that alternates between at least a first target pressure and a second target pressure, the second target pressure being different from the first target pressure, and wherein in the process of circulating the culture solution, the culture solution is made to flow out of the holder after the process of applying the pressure, and then drawn into the holder after flowing out of the holder, wherein in the process of applying the pressure, the shut-off valve part is closed by the shut-off valve drive unit receiving a control output generated by the processor and the external pressure is applied from the pressure generator unit via the pressure circuit through the pressure transmission part to the holder, so that the pressure in the holder alternates between a first pressurization in which the pressure in the holder reaches and maintains the first target pressure and a second pressurization in which the pressure in the holder reaches and maintains the second target pressure, wherein after alternating between the first pressurization and the second pressurization, the process of applying the pressure moves to the process of circulating the culture solution, wherein in the process of circulating the culture solution, the shut-off valve part is released by the shut-off valve drive unit receiving the control output generated by the processor, and wherein in a process of making the culture solution flow out of the holder during the process of circulating the culture solution, the external pressure is applied from the pressure generator unit via the pressure circuit through the pressure transmission part to the culture solution in the holder with the first valve in a closed state and the second valve in an open state for making the culture solution in the holder flow into a downstream side of the culture solution circuit, wherein in a process of drawing the culture solution into the holder during the process of circulating the culture solution, the external pressure, which is applied from the pressure generator unit via the pressure circuit through the pressure transmission part to the holder, is reduced with the first valve in an open state and the second valve in a closed state, so as to draw the culture solution from a culture solution reservoir side into the holder, wherein the culture unit main body of the pressure and circulation culture apparatus is separable from the culture unit at the shut-off valve part and the pressure transmission part, and wherein the cultured object is transportable as a unit with the culture unit main body by making the culture unit main body separate from the culture unit at the shut-off valve part and the pressure transmission part after culture of the culture object.

4. The pressure and circulation culture system of claim 3, wherein a pressure transmission space that stores the culture solution is formed in the pressure transmission part, wherein the pressure transmission part comprises an external pressure operation part which applies the external pressure on a pressure transmission film that is disposed between the pressure transmission space and the external pressure operation part, and wherein the pressure transmission film is reciprocated by applying and reducing the external pressure, and the external pressure is transmitted to the culture solution.

* * * * *